(12) United States Patent
Ekblad et al.

(10) Patent No.: US 10,155,792 B2
(45) Date of Patent: Dec. 18, 2018

(54) ALBUMIN BINDING POLYPEPTIDE

(71) Applicant: AFFIBODY AB, Solna (SE)

(72) Inventors: Caroline Ekblad, Saltsjö-Boo (SE); Joachim Feldwisch, Tyresö (SE); Kyong-Hoon Ahn, Seoul (KR)

(73) Assignee: AFFIBODY AB, Solna (SE)

( * ) Notice: Subject to any disclaimer, the term of this patent is extended or adjusted under 35 U.S.C. 154(b) by 406 days.

(21) Appl. No.: 14/427,102

(22) PCT Filed: Sep. 25, 2013

(86) PCT No.: PCT/EP2013/069946
§ 371 (c)(1),
(2) Date: Mar. 10, 2015

(87) PCT Pub. No.: WO2014/048977
PCT Pub. Date: Apr. 3, 2014

(65) Prior Publication Data
US 2015/0225464 A1  Aug. 13, 2015

Related U.S. Application Data

(60) Provisional application No. 61/705,223, filed on Sep. 25, 2012.

(30) Foreign Application Priority Data

Sep. 25, 2012 (EP) ..................... 12185874

(51) Int. Cl.
| C07K 14/195 | (2006.01) |
| A61K 38/00 | (2006.01) |
| C07K 14/315 | (2006.01) |
| A61K 47/48 | (2006.01) |

(52) U.S. Cl.
CPC ...... *C07K 14/195* (2013.01); *A61K 47/48246* (2013.01); *C07K 14/315* (2013.01); *C07K 2319/00* (2013.01); *C07K 2319/31* (2013.01)

(58) Field of Classification Search
CPC ............ A61K 47/48246; C07K 14/195; C07K 14/315; C07K 2319/00; C07K 2319/31
See application file for complete search history.

(56) References Cited

U.S. PATENT DOCUMENTS

| 6,362,225 | B1 | 3/2002 | Andreakos |
| 7,288,265 | B1 | 10/2007 | Rolf |
| 9,211,344 | B2 | 12/2015 | Eckblad et al. |
| 2003/0017203 | A1 | 1/2003 | Crotts et al. |
| 2004/0001827 | A1 | 1/2004 | Dennis |
| 2005/0215475 | A1 | 9/2005 | Ong et al. |
| 2005/0282756 | A1 | 12/2005 | Mehta et al. |
| 2007/0134279 | A1 | 6/2007 | Stern |
| 2009/0163408 | A1 | 6/2009 | Fogelman et al. |
| 2011/0014247 | A1 | 1/2011 | Kidron |
| 2011/0142800 | A1 | 6/2011 | Kidron et al. |
| 2013/0034597 | A1 | 2/2013 | Maggio |
| 2014/0162956 | A1 | 6/2014 | Ekblad |
| 2014/0256621 | A1* | 9/2014 | Erickson ............ A61K 38/22 514/5.3 |
| 2015/0098991 | A1 | 4/2015 | Bejker et al. |
| 2016/0009767 | A9 | 1/2016 | Bejker et al. |
| 2016/0108095 | A1 | 4/2016 | Ekblad et al. |

FOREIGN PATENT DOCUMENTS

| CN | 101294187 A | 10/2008 |
| WO | 9101743 A1 | 2/1991 |
| WO | 9519374 A1 | 7/1995 |
| WO | 0145746 A2 | 6/2001 |
| WO | 2005087797 A1 | 9/2005 |
| WO | 2008043821 A1 | 4/2008 |
| WO | 2009016043 A2 | 2/2009 |
| WO | 2009080811 A1 | 7/2009 |
| WO | 2010054699 A1 | 5/2010 |
| WO | 2010141329 A1 | 12/2010 |
| WO | 2012004384 A2 | 1/2012 |
| WO | 2012016043 A2 | 2/2012 |
| WO | 2012050930 A2 | 4/2012 |
| WO | 2013009539 A1 | 1/2013 |
| WO | 2015091957 A1 | 6/2015 |

OTHER PUBLICATIONS

Russelllab, Lysine, Arginine pp. 1-4, published online, Feb. 1, 2002.*
De Chateau, M., "Protein FAB, a Mosaic Albumin-binding Bacterial Protein Representing the First Contemporary Example of Modulue Shuffling", The Journal of Biological Chemistry, Apr. 22, 1994; vol. 269 (16) pp. 12147-12151.
Goetsch et al. "Identification of B- and T-Cell Epitopes of BB, a Carrier Protein Derived from the G Protein of *Streptococcus* Strain G148" Clinical and Diagnostic Laboratory Immunology; vol. 10, No. 1; Jan. 2003, pp. 125-132.
He et al., "An Artifically Evolved Albumin Binding Module Facilitates Chemical Shift Epitope Maping of GA Domain Interactions with Phylogenetically Diverse Albumins" The Protein Society, vol. 16, (2007) pp. 1490-1494.
Jonsson; "Engineering of a femtomolar affinity binding protein to human serum albumin"; Protein Engineering, Design & Selection, vol. 21, No. 8; 2008; pp. 515-527.

(Continued)

*Primary Examiner* — Rachael E Bredefeld
*Assistant Examiner* — Erinne R Dabkowski
(74) *Attorney, Agent, or Firm* — Cantor Colburn LLP

(57) ABSTRACT

The present disclosure relates to a class of engineered polypeptides having a binding affinity for albumin. In particular, the present invention relates to albumin binding polypeptides which have a high resistance to enzymatic cleavage. The disclosure provides an albumin binding polypeptide comprising an albumin binding motif, which motif consists of the amino acid sequence GVSDFYKKLI $X_a$KAKTVEGVE ALKX$_b$X$_c$I (SEQ ID NO:29).

24 Claims, 12 Drawing Sheets

Specification includes a Sequence Listing.

(56) References Cited

OTHER PUBLICATIONS

Sletten et al.; "Bioorthogonal Chemistry: Fishing for Selectivity in a Sea of Functionality"; Angew Chem Int Ed Engl., 48(38); 2009; 6974-6998.
Sosabowski et al.; "Conjugation of DOTA-like chelating agents to peptides and radiolabeling with trivalent metallic isotopes"; Nature Protocols, vol. 1, No. 2; 2006; 972-976.
Tanaka et al.; "N-Terminal glycine-specific protein conjugation catalyzed by microbial transglutaminase"; FEBS Letters; 579; 2005; 2092-2096.
The online Medical Dictionary; "Definition of Derivative"; accessed on Jul. 7, 2005; 3 pages.
International Search Report of the International Searching Authority for International Patent Application No. PCT/EP2013/069949; International Filing Date: Sep. 25, 2013; dated Nov. 11, 2013; 3 Pages.
Tanaka et al., "High-level Production and Purification of Clostripain Expressed in a Virulence-Attenuated Strain of Clostridium Perfringens", oProtein Expression and Purification; 76 (2011); pp. 83-89.
Yanan et al., "An Artificially Evolved Albumin Binding Module Facilitates Chemical Shift Epitope Mapping of GA Domain Interactions with Phylogenetically Diverse Albumins", Protein Science; 16; (2007); pp. 1490-1494.
IPRP and Written Opinion of the International Searching Authority for International Patent Application No. PCT/EP2013/069946; International Filing Date: Sep. 9, 25, 2013; dated Apr. 9, 2015; 5 Pages.
Labouesse "The Hydrolysis of Glucagon by Clostripain" Bulletin de la Societe de Chimie Biologique; 42(11); (1960); pp. 1293-1304. With English Abstract.
Labrou et al., "The Structure-Function Relationship in the Clostripain Family of Peptidases", Eur. J. Biochem. 271; (2004); pp. 983-992.
Mitchell et al., "Purification and Properties of Clostridiopeptidase B (Clostripain)", The Journal of Biological Chemistry; vol. 243; No. 18; (1968); pp. 4683-4692.
Frye, C.A., et al., "P-3-BSA, but not P-11-PSA, implants in the VTA rapidly facilitate receptivity in hamsters after progesterone priming to the VMH", Behavioural Brain Research, 53 (1993) pp. 167-175.
Strohl, William R., "Fusion Proteins for Half-Life Extension of Biologics as a Strategy to Make Biobetters", BioDrugs (2015) 29 pp. 215-239.
Aboud-Pirak, E. et al., "Cytotoxic Activity of Daunorubicin or Vindesin Conjugated to a Monoclonal Antibody on Cultured MCF-7 Breast Carcinoma Cells", Biochemical Pharmacology, vol. 38, No. 4, (1989) pp. 641-648.
Bauss, F. et al., "Effect of 17B-Estradiol-Bisphosphonate Conjugates, Potential Bone-Seeking Estrogen Pro-Drugs, on 17B-Estradiol Serum Kinetics and Bone Mass in Rats", Calcif Tissue Int (1996) 59, pp. 168-173.
Bonora, G.M. et al., "Antisense activity of an anti-HIV oligonucleotide conjugated to linear and branched high molecular weight polyethylene glycols", Il Farmaco 53 (1998), pp. 634-637.
Guo, Neng-Hua et al., "Antiproliferative and antitumor activities of D-reverse peptides derived from the second type-1 repeat of thrombospondin-1", J. Peptide Res. 50, 1997, pp. 210-221.
Langer, M. et al., "Novel Peptide Conjugates for Tumor-Specific Chemotherapy", J. Med. Chem. 2001, 44, pp. 1341-1348.
Parker, Andrew S. et al., "Optimization algorithms for functional deimmunization of therapeutic proteins", BMC Bioinformatics 2010, 11:180; pp. 1-15.
Qui, Y. et al., "Oestrogen-induced apoptosis in colonocytes expressing oestrogen receptor B", Journal of Endocrinology (2002) 174, pp. 369-377.

\* cited by examiner

Figure 1

| Designation | Amino acid sequence | SEQ ID NO: |
|---|---|---|
| | GVSDFYKKLIDKAKTVEGVEALKDAI | SEQ ID NO:1 |
| | GVSDFYKKLIDKAKTVEGVEALKDEI | SEQ ID NO:2 |
| | GVSDFYKKLIDKAKTVEGVEALKEAI | SEQ ID NO:3 |
| | GVSDFYKKLIDKAKTVEGVEALKEEI | SEQ ID NO:4 |
| | GVSDFYKKLIEKAKTVEGVEALKDAI | SEQ ID NO:5 |
| | GVSDFYKKLIEKAKTVEGVEALKDEI | SEQ ID NO:6 |
| | GVSDFYKKLIEKAKTVEGVEALKEAI | SEQ ID NO:7 |
| | GVSDFYKKLIEKAKTVEGVEALKEEI | SEQ ID NO:8 |
| | LAEAKEAANAELDSYGVSDFYKKLIDKAKTVEGVEALKDAILAALP | SEQ ID NO:9 |
| | LAEAKEAANAELDSYGVSDFYKKLIDKAKTVEGVEALKDEILAALP | SEQ ID NO:10 |
| | LAEAKEAANAELDSYGVSDFYKKLIDKAKTVEGVEALKEAILAALP | SEQ ID NO:11 |
| | LAEAKEAANAELDSYGVSDFYKKLIDKAKTVEGVEALKEEILAALP | SEQ ID NO:12 |
| | LAEAKEAANAELDSYGVSDFYKKLIEKAKTVEGVEALKDAILAALP | SEQ ID NO:13 |
| | LAEAKEAANAELDSYGVSDFYKKLIEKAKTVEGVEALKDEILAALP | SEQ ID NO:14 |
| | LAEAKEAANAELDSYGVSDFYKKLIEKAKTVEGVEALKEAILAALP | SEQ ID NO:15 |
| | LAEAKEAANAELDSYGVSDFYKKLIEKAKTVEGVEALKEEILAALP | SEQ ID NO:16 |
| PEP12380 | GSSLAEAKEAANAELDSYGVSDFYKKLIDKAKTVEGVEALKDAILAALP | SEQ ID NO:17 |
| | GSSLAEAKEAANAELDSYGVSDFYKKLIDKAKTVEGVEALKDEILAALP | SEQ ID NO:18 |
| | GSSLAEAKEAANAELDSYGVSDFYKKLIDKAKTVEGVEALKEAILAALP | SEQ ID NO:19 |
| | GSSLAEAKEAANAELDSYGVSDFYKKLIDKAKTVEGVEALKEEILAALP | SEQ ID NO:20 |
| | GSSLAEAKEAANAELDSYGVSDFYKKLIEKAKTVEGVEALKDAILAALP | SEQ ID NO:21 |
| | GSSLAEAKEAANAELDSYGVSDFYKKLIEKAKTVEGVEALKDEILAALP | SEQ ID NO:22 |
| | GSSLAEAKEAANAELDSYGVSDFYKKLIEKAKTVEGVEALKEAILAALP | SEQ ID NO:23 |
| | GSSLAEAKEAANAELDSYGVSDFYKKLIEKAKTVEGVEALKEEILAALP | SEQ ID NO:24 |
| PEP12381 | GSSLAEAKEAANAELDSYGVSDFYKSLIDKAKTVEGVEALKDAILAALP | SEQ ID NO:25 |
| PEP12379 | GSSLAEAKEAANAELDSYGVSDFYKNLIDKAKTVEGVEALKDAILAALP | SEQ ID NO:26 |
| PEP07843 | GSSLAEAKEAANAELDSYGVSDFYKRLIDKAKTVEGVEALKDAILAALP | SEQ ID NO:27 |
| PEP06923 | GSSLAEAKVLANRELDKYGVSDFYKRLINKAKTVEGVEALKLHILAALP | SEQ ID NO:28 |

PEP12379 HSA

PEP12380 HSA

PEP12381 HSA

PEP07843 HSA

PEP06923 HSA

ALBUMIN BINDING POLYPEPTIDE

CROSS-REFERENCE TO RELATED APPLICATIONS

This Application is a U.S. National Stage Application of PCT/EP2013/069946, filed Sep. 25, 2013, which claims priority to U.S. Provisional Patent Application No. 61/705,223, filed Sep. 25, 2012, both of which are incorporated by reference in their entireties.

TECHNICAL FIELD

The present invention relates to a class of engineered polypeptides having a binding affinity for albumin. In particular, the present invention relates to albumin binding polypeptides which have a high resistance to enzymatic cleavage.

BACKGROUND

Serum Albumin

Serum albumin is the most abundant protein in mammalian sera (40 g/l; approximately 0.7 mM in humans), and one of its functions is to bind molecules such as lipids and bilirubin (Peters T, Advances in Protein Chemistry 37:161, 1985). The half-life of serum albumin is directly proportional to the size of the animal, where for example human serum albumin (HSA) has a half-life of 19 days and rabbit serum albumin has a half-life of about 5 days (McCurdy T R et al, J Lab Clin Med 143:115, 2004). Human serum albumin is widely distributed throughout the body, in particular in the intestinal and blood compartments, where it is mainly involved in the maintenance of osmolarity. Structurally, albumins are single-chain proteins comprising three homologous domains and totaling 584 or 585 amino acids (Dugaiczyk L et al, Proc Natl Acad Sci USA 79:71, 1982). Albumins contain 17 disulfide bridges and a single reactive thiol, C34, but lack N-linked and 0-linked carbohydrate moieties (Peters, 1985, supra; Nicholson J P et al, Br J Anaesth 85:599, 2000). The lack of glycosylation simplifies recombinant expression of albumin. This property of albumin, together with the fact that its three-dimensional structure is known (He X M and Carter D C, Nature 358:209 1992), has made it an attractive candidate for use in recombinant fusion proteins. Such fusion proteins generally combine a therapeutic protein (which would be rapidly cleared from the body upon administration of the protein per se) and a plasma protein (which exhibits a natural slow clearance) in a single polypeptide chain (Sheffield W P, Curr Drug Targets Cardiovacs Haematol Disord 1:1, 2001). Such fusion proteins may provide clinical benefits in requiring less frequent injection and higher levels of therapeutic protein in vivo.

Fusion or Association with HSA Results in Increased In Vivo Half-Life of Proteins Serum albumin is devoid of any enzymatic or immunological function and, thus, should not exhibit undesired side effects upon coupling to a bioactive polypeptide. Furthermore, HSA is a natural carrier involved in the endogenous transport and delivery of numerous natural as well as therapeutic molecules (Sellers E M and Koch-Weser M D, "Albumin Structure, Function and Uses", eds Rosenoer V M et al, Pergamon, Oxford, p 159, 1977). Several strategies have been reported to either covalently couple proteins directly to serum albumins or to a peptide or protein that will allow in vivo association to serum albumins. Examples of the latter approach have been described e.g. in WO91/01743. This document describes inter alia the use of albumin binding peptides or proteins derived from streptococcal protein G for increasing the half-life of other proteins. The idea is to fuse the bacterially derived, albumin binding peptide/protein to a therapeutically interesting peptide/protein, which has been shown to have a rapid clearance in blood. The thus generated fusion protein binds to serum albumin in vivo, and benefits from its longer half-life, which increases the net half-life of the fused therapeutically interesting peptide/protein.

Association with HSA Results in Decreased Immunogenicity

In addition to the effect on the in vivo half-life of a biologically active protein, it has been proposed that the non-covalent association with albumin of a fusion between a biologically active protein and an albumin binding protein acts to reduce the immune response to the biologically active protein. Thus, in WO2005/097202, there is described the use of this principle to reduce or eliminate the immune response to a biologically active protein.

Albumin Binding Domains of Bacterial Receptor Proteins

Streptococcal protein G is a bi-functional receptor present on the surface of certain strains of streptococci and capable of binding to both IgG and serum albumin (Björck et al, Mol Immunol 24:1113, 1987). The structure is highly repetitive with several structurally and functionally different domains (Guss et al, EMBO J 5:1567, 1986), more precisely three Ig-binding motifs and three serum albumin binding domains (Olsson et al, Eur J Biochem 168:319, 1987). The structure of one of the three serum albumin binding domains has been determined, showing a three-helix bundle domain (Kraulis et al, FEBS Lett 378:190, 1996). This motif was named ABD (albumin binding domain) and is 46 amino acid residues in size. In the literature, it has subsequently also been designated G148-GA3.

Other bacterial albumin binding proteins than protein G from *Streptococcus* have also been identified, which contain domains similar to the albumin binding three-helix domains of protein G. Examples of such proteins are the PAB, PPL, MAG and ZAG proteins. Studies of structure and function of such albumin binding proteins have been carried out and reported e.g. by Johansson and co-workers (Johansson et al, J Mol Biol 266:859-865, 1997; Johansson et al, J Biol Chem 277:8114-8120, 2002), who introduced the designation "GA module" (protein G-related albumin binding module) for the three-helix protein domain responsible for albumin binding. Furthermore, Rozak et al have reported on the creation of artificial variants of the GA module, which were selected and studied with regard to different species specificity and stability (Rozak et al, Biochemistry 45:3263-3271, 2006; He et al, Protein Science 16:1490-1494, 2007). In the present disclosure, the terminology with regard to GA modules from different bacterial species established in the articles by Johansson et al and by Rozak et al will be followed.

Recently, variants of the G148-GA3 domain have been developed, with various optimized characteristics. Such variants are for example disclosed in PCT publications WO2009/016043 and WO2012/004384.

Clostripain

Clostripain, also known as endoproteinase Arg-C, is a two-chain proteinase that can be isolated from *Clostridium histolyticum*. Clostripain has been shown to have both proteolytic and amidase/esterase activity (Mitchell, et al (1968), J Biol Chem 243:4683-4692). Clostripain activity has been reported to be optimal in the pH range of 7.6-7.9.

Clostripain preferentially cleaves at the carboxyl group of arginine residues (Labrou et al (2004), Eur J Biochem 271(5):983-92; Keil (1992), "Specificity of proteolysis", Springer-Verlag, pp 335), however the cleavage of lysyl bonds has also been reported. Clostripain has been shown to accept substrates containing Lys instead of Arg, however reaction rates are low in comparison to reactions with Arg containing substrates. For example, clostripain has been reported to cleave glucagon at Arg-Arg, Arg-Ala and the Lys-Tyr sites. The relative initial rates of hydrolysis of these three bonds are 1, 1/7 and 1/300 (Labouesses (1960), Bull Soc Chim Biol 42:1293-304).

Clostripain cleavage is frequently utilized in biomedical and biotechnological applications. Applications of clostripain cleavage include peptide mapping, sequence analysis, cell isolation, hydrolysis/condensation of amide bonds, and peptide synthesis.

Clostripain may for example be used in order to cleave off tags (such as $His_6$, c-Myc, Flag and GST tags) used for protein purification and/or detection. Additionally, clostripain cleavage may be used during the production of amidated therapeutic polypeptides from a precursor polypeptide, whereby the resistance of the therapeutic polypeptide to proteolytic degradation by endogenous proteases upon administration to animal or human subjects is increased.

As evident from the different sections of this background description, the provision of polypeptide molecules with a high affinity for albumin and exhibiting high resistance to enzymatic cleavage, in particular by clostripain, is a key factor in the development of various biomedical, biotechnological and other applications, and there is therefore a need in the art of such polypeptide molecules.

DISCLOSURE OF THE INVENTION

The first aspect of the invention meets the need for novel polypeptides with a comparably high albumin affinity and high resistance to clostripain cleavage, through the provision of an albumin binding polypeptide comprising an albumin binding motif (BM), which motif consists of the amino acid sequence:

```
GVSDFYKKLI XaKAKTVEGVE ALKXbXcI (SEQ ID NO:29)
``` wherein, independently of each other,
$X_a$ is selected from D and E;
$X_b$ is selected from D and E; and
$X_c$ is selected from A and E.

In one embodiment of the polypeptide according to this aspect of the invention, $X_a$ is D.

In one embodiment of the polypeptide according to this aspect of the invention, $X_b$ is D.

In one embodiment of the polypeptide according to this aspect of the invention, $X_c$ is A.

Taking all the above combinations in account, it is clear that the sequence of the albumin binding motif BM is selected from the group consisting of SEQ ID NO:1-8. In one embodiment of the polypeptide according to this aspect of the invention, the sequence of the BM is SEQ ID NO:1.

In order to provide albumin binding polypeptides, comprising the albumin binding domain (ABD) or variants thereof, which peptides are highly resistant to cleavage by clostripain, the inventors have studied variants of PEP07843 (SEQ ID NO:27). The inventors show that substitution of the arginine residue (R) by a lysine residue (K) in a position of PEP07843 corresponding to position 8 in the BM as defined herein, exhibits unexpectedly superior properties with respect to protease stability as compared to other variants, wherein the arginine residue at this position has been substituted by amino acids which, in contrast to lysine, have not been previously described as sites of clostripain cleavage (see Example 3 and FIG. 3).

Hence, the finding that the Arg-to-Lys substitution mutation discussed above stabilizes and improves the resistance of albumin binding polypeptide to clostripain cleavage is surprising and unexpected in the light of previous studies showing that clostripain cleaves peptides at the carboxyl group of Lys residues.

In one embodiment of this aspect of the present invention, there is provided an albumin binding polypeptide wherein the albumin binding motif forms part of a three-helix bundle protein domain. For example, the BM may essentially constitute or form part of two alpha helices with an interconnecting loop, within said three-helix bundle protein domain.

In particular embodiments of the invention, such a three-helix bundle protein domain is selected from the group consisting of three-helix domains of bacterial receptor proteins. Non-limiting examples of such bacterial receptor proteins may be selected from the group consisting of albumin binding receptor proteins from species of *Streptococcus*, *Peptostreptococcus* and *Finegoldia*, such as for example selected from the group consisting of proteins G, MAG, ZAG, PPL and PAB.

In a specific embodiment of the invention, the BM forms part of a domain of protein G, such as for example a domain of protein G from *Streptococcus* strain G148. In different variants of this embodiment, the three-helix bundle protein domain of which the BM forms a part is selected from the group consisting of domain GA1, domain GA2 and domain GA3 of protein G from *Streptococcus* strain G148, in particular domain GA3.

In alternative embodiments, the BM forms part of one or more of the five three-helix domains of the bacterial receptor protein protein A from *Staphylococcus aureus*; i.e. the three-helix bundle protein domain is selected from the group consisting of protein A domains A, B, C, D and E. In other similar embodiments, the BM forms part of protein Z, derived from domain B of protein A from *Staphylococcus aureus*.

In embodiments of the present invention wherein the BM "forms part of" a three-helix bundle protein domain, this is understood to mean that the sequence of the BM is "inserted" into or "grafted" onto the sequence of the original three-helix bundle domain, such that the BM replaces a similar structural motif in the original domain. For example, without wishing to be bound by theory, the BM is thought to constitute two of the three helices of a three-helix bundle, and can therefore replace such a two-helix motif within any three-helix bundle. As the skilled person will realize, the replacement of two helices of the three-helix bundle domain by the two BM helices has to be performed so as not to affect the basic structure of the polypeptide. That is, the overall folding of the Ca backbone of the polypeptide according to this embodiment of the invention will be substantially the same as that of the three-helix bundle protein domain of which it forms a part, e.g. having the same elements of secondary structure in the same order etc. Thus, a BM according to the invention "forms part" of a three-helix bundle domain if the polypeptide according to this embodiment of the invention has the same fold as the original domain, implying that the basic structural properties are shared, those properties e.g. resulting in similar CD spectra. The skilled person is aware of other parameters that are relevant.

In one embodiment of this aspect of the invention, the albumin binding polypeptide is a three-helix bundle protein domain, which comprises the albumin binding motif as defined above and additional sequences making up the remainder of the three-helix configuration. Thus, in one embodiment there is provided an albumin binding polypeptide which comprises the amino acid sequence:

(SEQ ID NO:30)
LAX$_3$ AKX$_6$ X$_7$ ANX$_{10}$ ELDX$_{14}$ Y-[BM]-LX$_{43}$ X$_{44}$ LP wherein
[BM] is an albumin binding motif as defined above, and, independently of each other,
X$_3$ is selected from C, E, Q and S;
X$_6$ is selected from C, E and S;
X$_7$ is selected from A and S;
X$_{10}$ is selected from A, R and S;
X$_{14}$ is selected from A, C, K and S;
X$_{43}$ is selected from A and K; and
X$_{44}$ is selected from A, E and S.

In one specific embodiment of this albumin binding polypeptide, X$_3$ is E.

In one specific embodiment of this albumin binding polypeptide, X$_6$ is E.

In one specific embodiment of this albumin binding polypeptide, X$_7$ is A.

In one specific embodiment of this albumin binding polypeptide, X$_{10}$ is A.

In one specific embodiment of this albumin binding polypeptide, X$_{14}$ is S.

In one specific embodiment of this albumin binding polypeptide, X$_{43}$ is A.

In one specific embodiment of this albumin binding polypeptide, X$_{44}$ is A.

As the skilled person will realize, the function of any polypeptide, such as the albumin binding capacity of the polypeptides according to the invention, is dependent on the tertiary structure of the polypeptide. It may therefore possible to make minor changes to the sequence of amino acids in a polypeptide without affecting the function thereof. Thus, the invention encompasses modified variants of the BM, which are such that the albumin binding characteristics and the high resistance to clostripain cleavage are retained. For example, it may be possible that an amino acid residue belonging to a certain functional grouping of amino acid residues (e.g. hydrophobic, hydrophilic, polar etc) could be exchanged for another amino acid residue from the same functional group.

As described in detail in the experimental section to follow, the inventors have identified individual albumin binding polypeptide sequences. These sequences constitute individual embodiments of the albumin binding polypeptide according to the first aspect of the present invention. The sequences of these individual albumin binding polypeptides are presented in FIG. 1 and as SEQ ID NO:9-16.

Thus, in one embodiment of the present invention according to this first aspect, there is provided an albumin binding polypeptide comprising an amino acid sequence selected from SEQ ID NO:9-16. Also encompassed by the present invention is an albumin binding polypeptide comprising an amino acid sequence with 93% or greater identity to a sequence selected from SEQ ID NO:9-16, provided that the amino acid in the position corresponding to position 23 in SEQ ID NO:9-16 is K. In some embodiments, the inventive polypeptide may comprise a sequence which is at least 94%, at least 95%, at least 96%, at least 97%, at least 98% or at least 99% identical to the sequence selected from SEQ ID NO:9-16, provided that the amino acid in the position corresponding to position 23 in SEQ ID NO:9-16 is K.

In one particular embodiment, the albumin binding polypeptide comprises a sequence selected from SEQ ID NO:9 and sequences having 93% or greater identity thereto, provided that the amino acid in the position corresponding to position 23 in SEQ ID NO:9 is K. In some embodiments, the inventive polypeptide may comprise a sequence which is at least 94%, at least 95%, at least 96%, at least 97%, at least 98% or at least 99 identical to SEQ ID NO:9, provided that the amino acid in the position corresponding to position 23 in SEQ ID NO:9 is K.

The term "% identity", as used throughout the specification, may be calculated as follows. The query sequence is aligned to the target sequence using the CLUSTAL W algorithm (Thompson et al, Nucleic Acids Research, 22: 4673-4680 (1994)). A comparison is made over the window corresponding to the shortest of the aligned sequences. The shortest of the aligned sequences may in some instances be the target sequence. In other instances, the query sequence may constitute the shortest of the aligned sequences. The amino acid residues at each position are compared, and the percentage of positions in the query sequence that have identical correspondences in the target sequence is reported as % identity.

The terms "albumin binding" and "binding affinity for albumin" as used in this specification refer to a property of a polypeptide which may be tested for example by the use of surface plasmon resonance technology, such as in a Biacore instrument. For example as described in the examples below, albumin binding affinity may be tested in an experiment in which albumin, or a fragment thereof, is immobilized on a sensor chip of the instrument, and the sample containing the polypeptide to be tested is passed over the chip. Alternatively, the polypeptide to be tested is immobilized on a sensor chip of the instrument, and a sample containing albumin, or a fragment thereof, is passed over the chip. Albumin may, in this regard, be a serum albumin from a mammal, such as human serum albumin. The skilled person may then interpret the results obtained by such experiments to establish at least a qualitative measure of the binding affinity of the polypeptide for albumin. If a quantitative measure is desired, for example to determine a $K_D$ value for the interaction, surface plasmon resonance methods may also be used. Binding values may for example be defined in a Biacore2000 instrument (Biacore AB). Albumin is suitably immobilized on a sensor chip of the measurement, and samples of the polypeptide whose affinity is to be determined are prepared by serial dilution and injected in random order. $K_D$ values may then be calculated from the results using for example the 1:1 Langmuir binding model of the BIAevaluation 4.1 software, or other suitable software, provided by the instrument manufacturer (Biacore AB).

The albumin binding polypeptide according to this first aspect of the present invention binds to albumin such that the relative $K_D$ value of the interaction is at most $1 \times 10^{-9}$ M, i.e. 1 nM. In some embodiments, the $K_D$ value of the interaction is at most $1 \times 10^{-10}$ M, such as at most $1 \times 10^{-11}$ M, such as at most $1 \times 10^{-12}$ M, for example at most $1 \times 10^{-13}$ M, such as at most $1 \times 10^{-14}$ M.

In one embodiment of the invention, the albumin to which the albumin binding polypeptide binds is selected from human serum albumin, rat serum albumin, cynomolgus serum albumin and mouse serum albumin.

In one particular embodiment, the albumin to which the albumin binding polypeptide binds is human serum albumin.

The invention also encompasses an albumin binding polypeptide as described above, which further additionally comprises one or more amino acid(s) positioned on one or both sides of the albumin binding motif. These amino acid residues may play a role in enhancing the binding of albumin by the polypeptide, but may equally well serve other purposes, related for example to one or more of the production, purification, stabilization in vivo or in vitro, coupling or detection of the polypeptide, as well as any combination thereof.

The amino acids directly preceding or following the alpha helix at the N or C terminus of the amino acid sequence as defined herein may thus in one embodiment affect the conformational stability. One example of an amino acid residue which may contribute to improved conformational stability is a serine residue positioned at the N terminal of said amino acid sequence. The N-terminal serine residue may in some cases form a canonical S-X-X-E capping box, by involving hydrogen bonding between the gamma oxygen of the serine side chain and the polypeptide backbone NH of the glutamic acid residue. This N-terminal capping may contribute to stabilization of the first alpha helix of the three helix domain which in some embodiments comprises the albumin binding motif.

Thus, in one embodiment of this aspect of the present invention, there is provided an albumin binding polypeptide which additionally comprises at least one serine residue at the N-terminal side of the polypeptide sequence as defined herein. The amino acid sequence is in other words preceded by one or more serine residue(s). Furthermore, the albumin binding polypeptide may additionally comprises one, two or three or more serine residues at either, or both of, the N-terminal or the C-terminal side of said polypeptide.

In one embodiment of this aspect of the present invention, there is provided an albumin binding polypeptide which additionally comprises a glycine residue at the N-terminal side of the polypeptide sequence as defined herein.

It is understood that the amino acid sequence as defined herein may be preceded by one, two, three, four or any suitable number of amino acid residues. Thus, the amino acid sequence may be preceded by a single serine residue, a single glycine residue or a combination of the two, such as a glycine-serine (GS) combination or a glycine-serine-serine (GSS) combination.

Thus, in one embodiment, there is provided an albumin binding polypeptide which additionally comprises the amino acids GS at the N-terminal side of the polypeptide sequence as defined herein.

In one particular embodiment, there is provided an albumin binding polypeptide which additionally comprises the amino acids GSS at the N-terminal side of the polypeptide sequence as defined herein.

In particular, the invention encompasses sequences of the individual albumin binding polypeptides presented in FIG. 1 as SEQ ID NO:17-24, such as SEQ ID No:17. These sequences constitute individual embodiments of the albumin binding polypeptide according to the above embodiment of the first aspect of the present invention.

In yet another embodiment, the additional amino acid residues comprise a glutamic acid at the N-terminal side of the polypeptide sequence as defined herein.

Similarly, C-terminal capping may be exploited to improve stability of the third alpha helix in a three helix domain comprising the albumin binding motif, when such a three helix domain is present.

A proline residue when present at the C-terminal side of the amino acid sequence as defined herein may at least partly function as a capping residue. In such a case, a lysine residue following the proline residue at the C-terminal side may contribute to further stabilization of the third helix of the albumin binding polypeptide, by hydrogen bonding between the epsilon amino group of the lysine residue and the carbonyl groups of the amino acids located two and three residues before the lysine in the polypeptide backbone.

Thus, in one embodiment, there is provided an albumin binding polypeptide which additionally comprises a lysine residue at the C-terminal side of the polypeptide sequence according to any one or more of the above definitions.

As discussed above, the additional amino acids may be related to the production of the albumin binding polypeptide. In particular, when an albumin binding polypeptide according to an embodiment in which a proline is present at the C terminus is produced by chemical peptide synthesis, one or more optional amino acid residues following the C-terminal proline may provide advantages. Such additional amino acid residues may for example prevent formation of undesired substances, such as diketopiperazine at the dipeptide stage of the synthesis. One example of such an amino acid residue is glycine.

Thus, in another embodiment, there is provided an albumin binding polypeptide which additionally comprises a glycine residue at the C-terminal side of the polypeptide sequence according to any one or more of the above definitions.

In one embodiment, the additional amino acids comprise a glycine residue at the C-terminal side of the polypeptide, directly following the proline residue or following an additional lysine and/or glycine residue as accounted for above.

Alternatively, polypeptide production may benefit from amidation of the C-terminal proline residue of the amino acid sequence as defined herein, when present. In this case, the C-terminal proline comprises an additional amine group at the carboxyl carbon. In one embodiment of the polypeptide described herein, particularly those ending at its C-terminus with proline or other amino acid known to racemize during peptide synthesis, the abovementioned addition of a glycine to the C-terminus or amidation of the proline, when present, can also counter potential problems with racemization of the C-terminal amino acid residue. If the polypeptide, amidated in this way, is intended to be produced by recombinant means, rather than by chemical synthesis, amidation of the C-terminal amino acid can be performed by several methods known in the art, e.g. through the use of amidating PAM enzyme.

The skilled person is aware of methods for accomplishing C-terminal modification, such as by different types of pre-made matrices for peptide synthesis.

Thus, the additional amino acid residues may comprise one or more amino acid residue(s) added for purposes of chemical coupling, e.g. to a chromatographic resin to obtain an affinity matrix or to a chelating moiety for complexing with a metal radionuclide. An example of this is the addition of a cysteine residue at the very first or very last position in the polypeptide chain, i.e. at the N or C terminus. Such additional amino acid residues may also comprise a "tag" for purification or detection of the polypeptide, such as a hexahistidyl ($His_6$) tag, or a glutathione S-transferase tag (GST-tag), or a "myc" ("c-Myc") tag or a "FLAG" tag for interaction with antibodies specific to the tag. The skilled person is aware of other alternatives.

The "additional amino acid residues" discussed above may also constitute one or more polypeptide domain(s) with any desired function, such as the same binding function as the first, albumin binding domain, or another binding function, or a therapeutic function, or a cytotoxic function, or an enzymatic function, or a fluorescent function, or mixtures thereof. Linked polypeptide "units" in a such a polypeptide according to the invention may be connected by covalent coupling using known organic chemistry methods, or expressed as one or more fusion polypeptides in a system for recombinant expression of polypeptides, or joined in any other fashion, directly or mediated by a linker comprising a number of amino acids.

In another embodiment, the additional amino acid residues comprise a cysteine residue at the N- and/or C-terminal of the polypeptide. Such a cysteine residue may directly precede and/or follow the amino acid sequence as defined herein or may precede and/or follow any other additional amino acid residues as described above. By the addition of a cysteine residue to the polypeptide chain, a thiol group for site directed conjugation of the albumin binding polypeptide may be obtained. Alternatively, a selenocysteine residue may be introduced at the C-terminal of the polypeptide chain to facilitate site-specific conjugation (Cheng et al, Nat Prot 1:2, 2006).

Thus, in another embodiment of this aspect of the present invention, there is provided an albumin binding polypeptide which additionally comprises a cysteine residue at the N-terminal side of the polypeptide sequence according to any one or more of the above definitions.

In another embodiment, there is provided an albumin binding polypeptide which additionally comprises a cysteine residue at the C-terminal side of the polypeptide sequence according to any one or more of the above definitions.

In one embodiment of this aspect of the present invention, there is provided an albumin binding polypeptide comprising no more than two cysteine residues, such as no more than one cysteine residue.

Furthermore, the invention also encompasses multimers of the polypeptide with affinity for albumin, i.e. polypeptide chains comprising at least two albumin binding polypeptides or fragments thereof as monomer units. It may be of interest, e.g. in a method of purification of albumin or in a therapeutic method exploiting the albumin binding function, to obtain even stronger binding of albumin than is possible with one polypeptide according to the invention. In this case, the provision of a multimer, such as a dimer, trimer or tetramer, of the polypeptide may provide the necessary avidity effects. The multimer may consist of a suitable number of polypeptides according to the invention. These polypeptide domains according to the invention, forming monomers in such a multimer, may all have the same amino acid sequence, but it is equally possible that they have different amino acid sequences. As described above, the linked polypeptide "units" in a multimer according to the invention may be connected by covalent coupling using known organic chemistry methods, or expressed as one or more fusion polypeptides in a system for recombinant expression of polypeptides, or joined in any other fashion, directly or mediated by a linker comprising a number of amino acids.

Additionally, "heterogenic" fusion polypeptides or proteins, or conjugates, in which an albumin binding polypeptide according to the invention, or multimer thereof, constitutes a first domain, or first moiety, and the second and further moieties have other functions than binding albumin, are also contemplated and fall within the ambit of the present invention. The second and further moiety/moieties of the fusion polypeptide or conjugate in such a protein suitably have a desired biological activity.

Thus, in a second aspect of the present invention, there is provided a fusion protein or a conjugate, comprising a first moiety consisting of an albumin binding polypeptide according to the first aspect, and a second moiety consisting of a polypeptide having a desired biological activity.

Non-limiting examples of such a desired biological activity comprise a therapeutic activity, a binding activity, and an enzymatic activity. In one embodiment, the second moiety having a desired biological activity is a therapeutically active polypeptide.

Non-limiting examples of therapeutically active polypeptides are biomolecules, such as molecules selected from the group consisting of human endogenous enzymes, hormones, growth factors, chemokines, cytokines and lymphokines. Non-limiting examples of therapeutically active biomolecules which may prove useful in a fusion or conjugate with the albumin binding polypeptide are selected from the group consisting of IL-2, GLP-1, BNP (Alb-beta-natriuretic peptide), IL-1-RA (interleukin-1 receptor antagonist), KGF (keratinocyte growth factor), Stemgen®, growth hormone (GH), G-CSF, CTLA-4, myostatin, Factor VII, Factor VIII, Factor IX and Factor X, and any combination or subgroup thereof.

Additional non-limiting examples of suitable biomolecules are non-human biologically active proteins, such as proteins selected from the group consisting of bacterial toxins (e.g. pseudomonas exotoxin and staphylococcal and streptococcal superantigens), enzymes (e.g. RNase and beta-lactamase) and activating proteins (e.g. streptokinase).

In another embodiment, there is provided a fusion protein or a conjugate wherein the second moiety having a desired biological activity is a binding polypeptide capable of selective interaction with a target molecule. The second and any further moieties are selected from binding moieties capable of selective interaction (binding) with a target molecule, typically a target molecule other than albumin even though albumin is not excluded.

Such a binding polypeptide may for example be selected from the group consisting of antibodies and fragments and domains thereof substantially retaining antibody binding activity; microbodies, maxybodies, avimers and other small disulfide-bonded proteins; and binding proteins derived from a scaffold selected from the group consisting of staphylococcal protein A and domains thereof, other three helix domains, lipocalins, ankyrin repeat domains, cellulose binding domains, γ crystallines, green fluorescent protein, human cytotoxic T lymphocyte-associated antigen 4, protease inhibitors such as Kunitz domains, PDZ domains, SH3 domains, peptide aptamers, staphylococcal nuclease, tendamistats, fibronectin type III domain, transferrin, zinc fingers and conotoxins.

In some embodiments, the target molecule for binding of said target binding polypeptide may be selected from the group consisting of amyloid R (AR) peptide of Alzheimer's disease; other disease-associated amyloid peptides; toxins, such as bacterial toxins and snake venoms; blood clotting factors, such as von Willebrand factor; interleukins, such as IL-13; myostatin; pro-inflammatory factors, such as TNF-α, TNF-α receptor, IL-1, IL-8 and IL-23; complement factors, such as C3 and C5; hypersensitivity mediators, such as histamine and IgE; tumor-related antigens, such as CD19, CD20, CD22, CD30, CD33, CD40, CD52, CD70, cMet, HER1, HER2, HER3, HER4, CAIX (carbonic anhydrase IX), CEA, IL-2 receptor, MUC1, PSMA, TAG-72; and other biological molecules such as G-CSF, GM-CSF, growth hormone (GH), insulin and somatostatin.

As the skilled person understands, the albumin binding polypeptide according to the first aspect may be useful in a fusion protein or as a conjugate partner to any other moiety. Therefore, the above lists of therapeutically active polypeptides, binding polypeptides and target molecules should not be construed as limiting in any way.

Other possibilities for the creation of fusion polypeptides or conjugates are also contemplated. Thus, an albumin binding polypeptide according to the first aspect of the invention may be covalently coupled to a second or further moiety or moieties, which in addition to or instead of target binding exhibit other functions. One example is a fusion between one or more albumin binding polypeptide(s) and an enzymatically active polypeptide serving as a reporter or effector moiety. Examples of reporter enzymes, which may be coupled to the albumin binding polypeptide to form a fusion protein, are known to the skilled person and include enzymes such as β-galactosidase, alkaline phosphatase, horseradish peroxidase and carboxypeptidase. Other options for the second and further moiety or moieties of a fusion polypeptide or conjugate according to the invention include, also without limitation, fluorescent polypeptides, such as green fluorescent protein, red fluorescent protein, luciferase and variants thereof.

In one embodiment of this aspect of the present invention, there is provided a fusion protein or conjugate, wherein the further moiety consists of a polypeptide having a further, desired biological activity, which may be the same as or different from that of the second moiety. In one particular embodiment, the second moiety may be selected from therapeutically active polypeptides, human endogenous enzymes, hormones, growth factors, chemokines, cytokines, lymphokines, IL-2, GLP-1, BNP, IL-1 receptor agonist, KGF, Stemgen®, GH, G-CSF, CTLA-4, myostatin, Factor VII, Factor VIII, Factor IX and Factor X and non-human biologically active proteins, selected from the group consisting of bacterial toxins, enzymes and activating proteins; and the further moiety may comprise a binding polypeptide capable of selective interaction with a target molecule as defined above. In another particular embodiment, the second and the further moiety each comprise a binding polypeptide capable of selective interaction with a target molecule as defined above.

With regard to the description herein of fusion proteins or conjugates incorporating an albumin binding polypeptide according to the invention, it is to be noted that the designation of first, second and further moieties is made for clarity reasons to distinguish between albumin binding polypeptide or polypeptides according to the invention on the one hand, and moieties exhibiting other functions on the other hand. These designations are not intended to refer to the actual order of the different domains in the polypeptide chain of the fusion protein or conjugate. Thus, for example, said first moiety may without restriction appear at the N-terminal end, in the middle, or at the C-terminal end of the fusion protein or conjugate.

In one embodiment of a conjugate according to the present disclosure, the second moiety is conjugated to the albumin binding polypeptide via a lysine or cysteine residue added to the N- or C-terminal of the albumin binding polypeptide or via a lysine or cysteine residue at a position within the albumin binding polypeptide in which they are present. If for example the albumin binding polypeptide comprises the sequence of 46 amino acids disclosed above, conjugation may be done at a position selected from $X_3$, $X_6$ and $X_{14}$. If the conjugation site is one within the amino acid sequence of the albumin binding polypeptide, such as a cysteine in position $X_{14}$ of the 46-mer, no additional amino acids need to be added to the albumin binding polypeptide for the purpose of enabling conjugation to the second moiety. Thus, in one embodiment of this aspect, there is provided a conjugate wherein the second moiety is conjugated to a first moiety via the thiol group of any cysteine residue present at a position of said first moiety corresponding to position $X_{14}$ of the disclosed 46-mer.

In a related aspect, there is provided an albumin binding polypeptide, fusion protein or conjugate as defined in the present disclosure, further comprising an organic molecule, such as a cytotoxic agent. Non-limiting examples of cytotoxic agents which may be fused or conjugated to an albumin binding polypeptide according to the first aspect, or combined with a fusion protein or conjugate according to the second aspect, are selected from calicheamycin, auristatin, doxorubicin, maytansinoid, taxol, ecteinascidin, geldanamycin, methotrexate and their derivatives, and combinations thereof. Previously, attempts have been made to treat various disorders with direct albumin conjugates. Such direct albumin conjugates have been exploited e.g. with doxorubicin in cancer (Kratz et al, J Med Chem 45: 5523-33, 2002) and metotrexate in rheumatoid arthritis (Wunder et al, J Immunol 170:4793-4801, 2003). It is to be understood that the albumin binding polypeptide, either by itself or as a moiety in a fusion protein or conjugate, by its high albumin binding ability provides an indirect means of construing albumin complexes, and thus may provide an alternative treatment option compared to the attempts mentioned above.

The above aspects furthermore encompass polypeptides in which the albumin binding polypeptide according to the first aspect, or the albumin binding polypeptide as comprised in a fusion protein or conjugate according to the second aspect, has been provided with a label group, such as a label selected from the group consisting of fluorescent dyes and metals, chromophoric dyes, chemiluminescent compounds and bioluminescent proteins, enzymes, radionuclides and particles, for example for purposes of detection of the polypeptide. In particular, the disclosure encompasses a radiolabeled polypeptide consisting of a radiochelate of an albumin binding polypeptide, fusion protein or conjugate as described herein and a radionuclide, such as a radioactive metal.

In embodiments where the labeled albumin binding polypeptide comprises an albumin binding polypeptide according to the first aspect of the disclosure and a label, the labeled polypeptide may for example be used for labeling serum albumin indirectly. Due to the strong association between the labeled polypeptide and serum albumin, the labeled polypeptide may be used for example to study vascular permeability and blood pool.

In other embodiments, the labeled albumin binding polypeptide is present as a moiety in a fusion protein or conjugate also comprising a second moiety having a desired biological activity. The label may in some instances be coupled only to the albumin binding polypeptide, and in some instances both to the albumin binding polypeptide and to the second moiety of the conjugate or fusion protein. Furthermore, it is also possible that the label may be coupled to a second moiety only and not the albumin binding moeity. Hence in yet another embodiment, there is provided an albumin binding polypeptide comprising a second moiety, wherein said label is coupled to the second moiety only. When reference is made to a labeled polypeptide, this should be understood as a reference to all aspects of polypeptides as described herein, including fusion proteins and conjugates comprising an albumin binding polypeptide and a second and optionally further moieties. Thus, a labeled polypeptide may contain only the albumin binding polypeptide and e.g. a therapeutic radionuclide, which may be chelated or covalently coupled to the albumin binding polypeptide, or contain the albumin binding polypeptide, a therapeutic radionuclide and a second moiety such as a small molecule having a desired biological activity, for example a therapeutic efficacy.

In embodiments where the albumin binding polypeptide, fusion protein or conjugate is radiolabeled, such a radiolabeled polypeptide may comprise a radionuclide. A majority of radionuclides have a metallic nature and metals are typically incapable of forming stable covalent bonds with elements presented in proteins and peptides. For this reason, labeling of proteins and peptides with radioactive metals is performed with the use of chelators, i.e. multidentate ligands, which form non-covalent compounds, called chelates, with the metal ions. In an embodiment of the albumin binding polypeptide, fusion protein or conjugate, the incorporation of a radionuclide is enabled through the provision of a chelating environment, through which the radionuclide may be coordinated, chelated or complexed to the polypeptide.

One example of a chelator is the polyaminopolycarboxylate type of chelator. Two classes of such polyaminopolycarboxylate chelators can be distinguished: macrocyclic and acyclic chelators.

In one embodiment, the albumin binding polypeptide, fusion protein or conjugate comprises a chelating environment provided by a polyaminopolycarboxylate chelator conjugated to the albumin binding polypeptide via a thiol group of a cysteine residue or an epsilon amine group of a lysine residue.

The most commonly used macrocyclic chelators for radioisotopes of indium, gallium, yttrium, bismuth, radioactinides and radiolanthanides are different derivatives of DOTA (1,4,7,10-tetraazacyclododecane-1,4,7,10-tetraacetic acid). In one embodiment, a chelating environment of the albumin binding polypeptide, fusion protein or conjugate is provided by DOTA or a derivative thereof. More specifically, in one embodiment, the chelating polypeptides encompassed by the present disclosure are obtained by reacting the DOTA derivative 1,4,7,10-tetraazacyclododecane-1,4,7-trisacetic acid-10-maleimidoethylacetamide (maleimidomonoamide-DOTA) with said polypeptide.

Additionally, 1,4,7-triazacyclononane-1,4,7-triacetic acid (NOTA) and derivatives thereof may be used as chelators. Hence, in one embodiment, there is provided an albumin binding polypeptide, fusion protein or conjugate, wherein the polyaminopolycarboxylate chelator is 1,4,7-triazacyclononane-1,4,7-triacetic acid or a derivative thereof.

The most commonly used acyclic polyaminopolycarboxylate chelators are different derivatives of DTPA (diethylenetriamine-pentaacetic acid). Hence, polypeptides having a chelating environment provided by diethylenetriaminepentaacetic acid or derivatives thereof are also encompassed by the present disclosure.

In a third aspect of the present invention, there is provided a polynucleotide encoding an albumin binding polypeptide or a fusion protein as described herein.

Also encompassed is a method of producing an albumin binding polypeptide or a fusion protein as described above, comprising expressing the polynucleotide, an expression vector comprising the polynucleotide and a host cell comprising the expression vector.

Also encompassed is a method of producing a polypeptide, comprising culturing said host cell under conditions permitting expression of said polypeptide from said expression vector, and isolating the polypeptide.

The albumin binding polypeptide of the present disclosure may alternatively be produced by non-biological peptide synthesis using amino acids and/or amino acid derivatives having protected reactive side-chains, the non-biological peptide synthesis comprising step-wise coupling of the amino acids and/or the amino acid derivatives to form a polypeptide according to the first aspect having protected reactive side-chains, removal of the protecting groups from the reactive side-chains of the polypeptide, and folding of the polypeptide in aqueous solution.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated for carrying out this invention, but that the invention will include all embodiments falling within the scope of the appended claims.

BRIEF DESCRIPTION OF THE FIGURES

FIG. 1 is a listing of the amino acid sequences of examples of albumin binding motifs comprised in albumin binding polypeptides of the invention (SEQ ID NO:1-8), examples of albumin binding polypeptides according to the invention (SEQ ID NO:9-24) and control polypeptides (SEQ ID NO:25 (PEP12381), 26 (PEP12379), 27 (PEP07843) and 28 (PEP06923)).

Figure 2A:
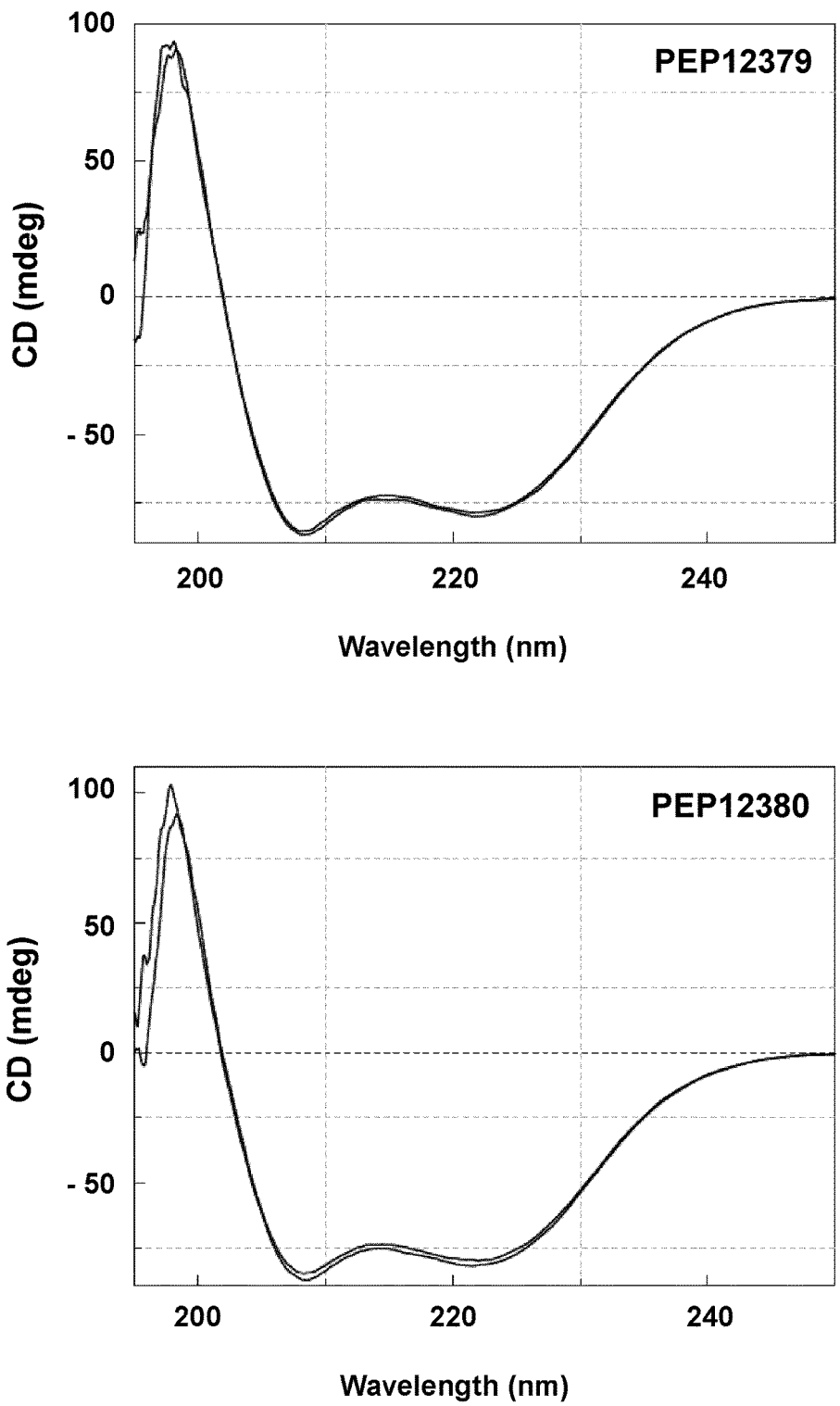
FIGS. 2A and 2B show the overlay of four CD spectra of the indicated albumin binding polypeptides PEP12379 (SEQ ID NO:26), PEP12380 (SEQ ID NO:17), PEP12381 (SEQ ID NO:25) and PEP07843 (SEQ ID NO:27), before and after heat treatment.

The invention will now be illustrated further through the non-limiting description of experiments conducted in accordance therewith. Unless otherwise specified, conventional chemistry and molecular biology methods were used throughout.

EXAMPLES

The aim of the study described below was to enable cleavage of fusion proteins containing an albumin binding domain with the enzyme clostripain (ArgC), without cleaving the protein within the albumin binding domain sequence. Herein, the inventors designed three variants of the albumin binding polypeptide PEP07843 (SEQ ID NO:27) and show that the inventive variant PEP12380 (SEQ ID NO:17), characterized by an Arg-to-Lys substitution, exhibits unexpectedly superior properties with respect to protease stability and albumin binding activity as compared to the other tested variants.

As used herein, the PEPXXXXX terminology refers to an albumin binding polypeptide having 46 amino acid residues, as defined in connection with the first aspect of the invention, as well as having a GSS extension on the N-terminal side. The numbering of amino acid positions thus refers to the positions of the amino acid residues within the above-mentioned 46 amino acid polypeptide, unless otherwise specified.

Example 1

Cloning, Expression and Purification of Albumin Binding Polypeptide Variants Summary In this example, three variants of the albumin binding polypeptide PEP07843 (SEQ ID NO:27), derived from the GA3 domain from protein G of *Streptococcus* strain G148, were created, substituting the single Arg in position 23 by another amino acid residue.

The three variants are as follows: PEP12379 (SEQ ID NO:26) with an R23N substitution, PEP12380 (SEQ ID NO:17) with an R23K substitution and PEP12381 (SEQ ID NO:25) with an R23S substitution.

The amino acid sequences of the polypeptides are listed in FIG. 1.

Cloning and Expression of ABD Variants

The ABD variants were cloned and expressed in *E. coli* using standard methods essentially as described in Example 1 in WO 2012/004384.

Analysis of ABD Variants

The obtained ABD variants were analyzed by SDS-PAGE. For the SDS-PAGE analysis, samples from cultivations and samples from finally purified albumin binding polypeptide variant were mixed with NuPAGE LDS Sample Buffer (Invitrogen), incubated at 70° C. for 15 min and loaded onto NuPAGE 4-12% Bis-Tris Gels (Invitrogen). The gels were run with NuPAGE MES SDS Running Buffer (Invitrogen) in an XCell II SureLock Electrophoresis Cell (Novex) employing the Sharp Prestained Standard (Invitrogen) as molecular weight marker and using PhastGel BlueR (GE Healthcare) for staining.

All ABD variants were purified by standard chromatography methods using affinity chromatography, reversed phase chromatography and size exclusion chromatography for buffer exchange essentially as described in Example 1 in WO 2012/004384.

Results

The expression analysis by SDS-PAGE showed that all ABD variants were soluble without any amount in the insoluble fraction. Purified proteins were stored in solution at −80° C. Freeze-thaw analysis showed good solubility of all ABD variants without visual detection of precipitations.

Example 2

Circular Dichroism Analysis

Summary

In this example, the secondary structure of the ABD variants obtained in Example 1 was analyzed, and their melting temperatures (Tm) were determined.

Secondary structure of ABD variants was analyzed by circular dichroism (CD) spectroscopy using a scan from 195-250 nm before and after the variable temperature measurement (see below). Purified albumin binding polypeptide variants were diluted in 1×PBS, to final concentration of 0.5 mg/ml. Circular dichroism (CD) analysis was performed on a Jasco J-810 spectropolarimeter in a cell with an optical path-length of 1 mm. Alpha helical proteins show typical minima at 208 and 222 nm.

Variable temperature measurement was used to determine the melting temperature, Tm. In these measurements, the absorbance was measured at 221 nm from 20° C. to 90° C., with a temperature slope of 5° C./min.

Results

The melting temperatures of the ABD variants were calculated by determining the midpoint of the transtition in the CD vs. temperature plot. The results are summarized in Table 2.

All three ABD variants show a Tm which is slightly reduced by 2-6° C. as compared to PEP07843. PEP12380 showed the highest thermal stability of the three variants (Table 2).

Figure 2B:
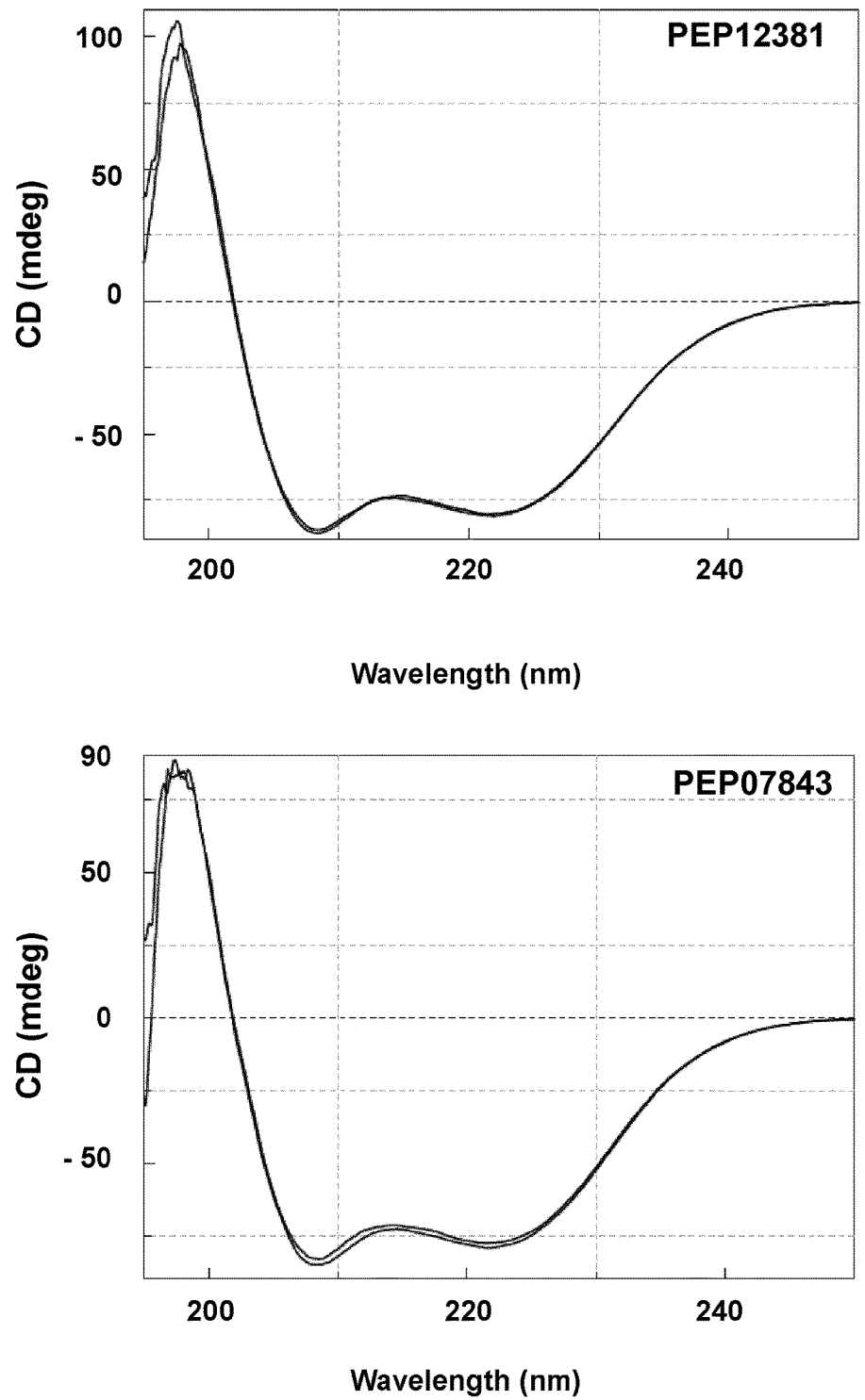

The CD spectra before and after heat treatment were compared in order to detect potential heat denaturation of the proteins. All ABD variants showed minima at 208 and 222 nm, as is typical for alpha helical proteins. They also exhibited identical spectra before and after heat treatment, indicating that the new ABD variants were not irreversibly denatured. FIGS. 2A and 2B show the CD spectra of the new ABD variants and of PEP07843 (SEQ ID NO:27) for comparison.

TABLE 2

| CD analysis of ABD variants | | |
| --- | --- | --- |
| Protein | Tm* | CD spectra overlay |
| PEP12379 | 56° C. | completely reversible |
| PEP12380 | 60° C. | completely reversible |
| PEP12381 | 56° C. | completely reversible |
| PEP07843 | 62° C. | completely reversible |

Example 3

Clostripain Cleavage

Summary

In order to assess clostripain cleavage of the ABD variants obtained in Example 1, the three new ABD variants and the control PEP07843 were incubated with clostripain, and the reactions stopped at fixed time points. The percentage remaining uncleaved ABD variant was analyzed by SDS-PAGE and LC/MS analysis (Example 4).

Clostripain Cleavage

Enzymatic digestion of PEP07843 and the three new variants was performed using clostripain from Worthington (No. LS001641) in 25 mM NaPi buffer pH 7.6, 150 mM NaCl, 1 mM CaAc, 2.5 mM DTT. Clostripain was dissolved freshly before initiation of the experiment.

In the first experiment, 0.2 U clostripain/mg ABD variant was incubated for up to 20 h at 25° C., but only a low level of cleavage was detected by SDS-PAGE and LC/MS analysis.

In the following experiment, the clostripain amount was increased to 5 U/mg ABD variant, and the samples were incubated for 0, 1, 2, 4, 6, 8 and 22 h at 25° C. in a thermomixer with mild shaking at 600 rpm.

Reactions were stopped by addition of 4×SDS sample buffer followed by incubation for 15 min at 70° C. (for SDS PAGE analysis) or by addition of trifluoroacetic acid (TFA) to a final concentration of 0.3%, which lowers the pH to approximately 2, and freezing at −80° C. (for LC/MS analysis).

Controls were reactions without clostripain and omitting DTT which prevents clostripain activity.

Figure 3:
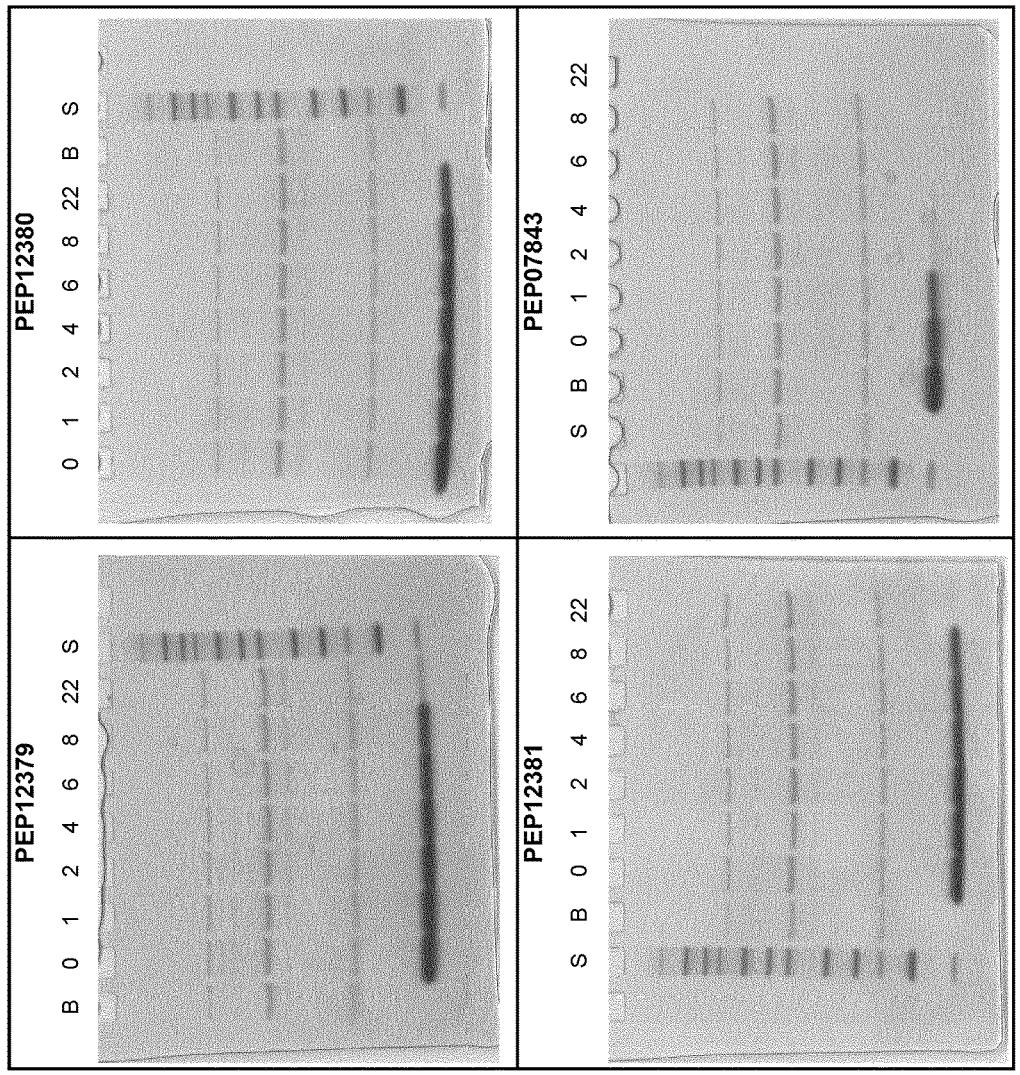
FIG. 3 shows the result of SDS-PAGE analysis of samples of the indicated albumin binding polypeptides, incubated for up to 22 h with clostripain.

Analysis of samples incubated with clostripain for up to 22 h was performed by SDS-PAGE using NuPAGE 4-12% gels from Invitrogen (see FIG. 3). In FIG. 3, lane S indicates sharp molecular weight marker standard (molecular weights 3.5, 10, 15, 20, 30, 40, 50, 60, 80, 110 and 160 kDa), lane B indicates a blank sample with clostripain but no ABD variant, and lanes 0-22 indicate ABD variant samples taken at the indicated incubation times in hours.

Results

The results are summarized in Table 3.

TABLE 3

Result of SDS-PAGE analysis

| Protein | Result |
| --- | --- |
| PEP12379 | some cleavage at 4-8 h and approximately 90% after 22 h |
| PEP12380 | some cleavage at 6-8 h and approximately 50% after 22 h |
| PEP12381 | some cleavage at 4-8 h and approximately 100% after 22 h |
| PEP07843 | approximately 75% cleaved after 2 h and 100% after 4-22 h |

Thus, after 2 h of clostripain incubation, approximately 75% of the PEP07843 polypeptide was cleaved, and after 4-22 h of incubation, 100 was cleaved. Variants PEP12379 (SEQ ID NO:26) and PEP12381 (SEQ ID NO:25) were both more resistant to clostripain cleavage as compared to PEP07843, but after 22 h of incubation approximately 90% and 100% of these variants, respectively, had been digested. PEP12380 (SEQ ID NO:17) showed the highest level of resistance to cleavage, as judged by the fact that only approximately 50% had been cleaved after 22 h of clostripain incubation.

Example 4

LC/MS Analysis

Summary

LC/MS-analysis of clostripain cleavage of the ABD variants obtained in Example 1 was performed at high and low enzyme concentrations and showed the gradual decrease of full-length peptide and increase of degradation products over time. The degradation products were identified by mass spectrometry.

LC/MS analyses were performed using an Agilent 1100 LC/MSD system, equipped with API-ESI and a single quadruple mass analyzer. 10 µl of each cleavage mixture was injected on a Zorbax 300SB-C8 Narrow-Bore column (2.1× 150 mm, 3.5 µm, Agilent Technologies) at a flow-rate of 0.5 ml/min. Elution was performed using a linear gradient of 10-70% solution B for 15 min at 0.5 ml/min. The separation was performed at 30° C. The ion signal and the absorbance at 280 and 220 nm were monitored.

Results

Figure 4:
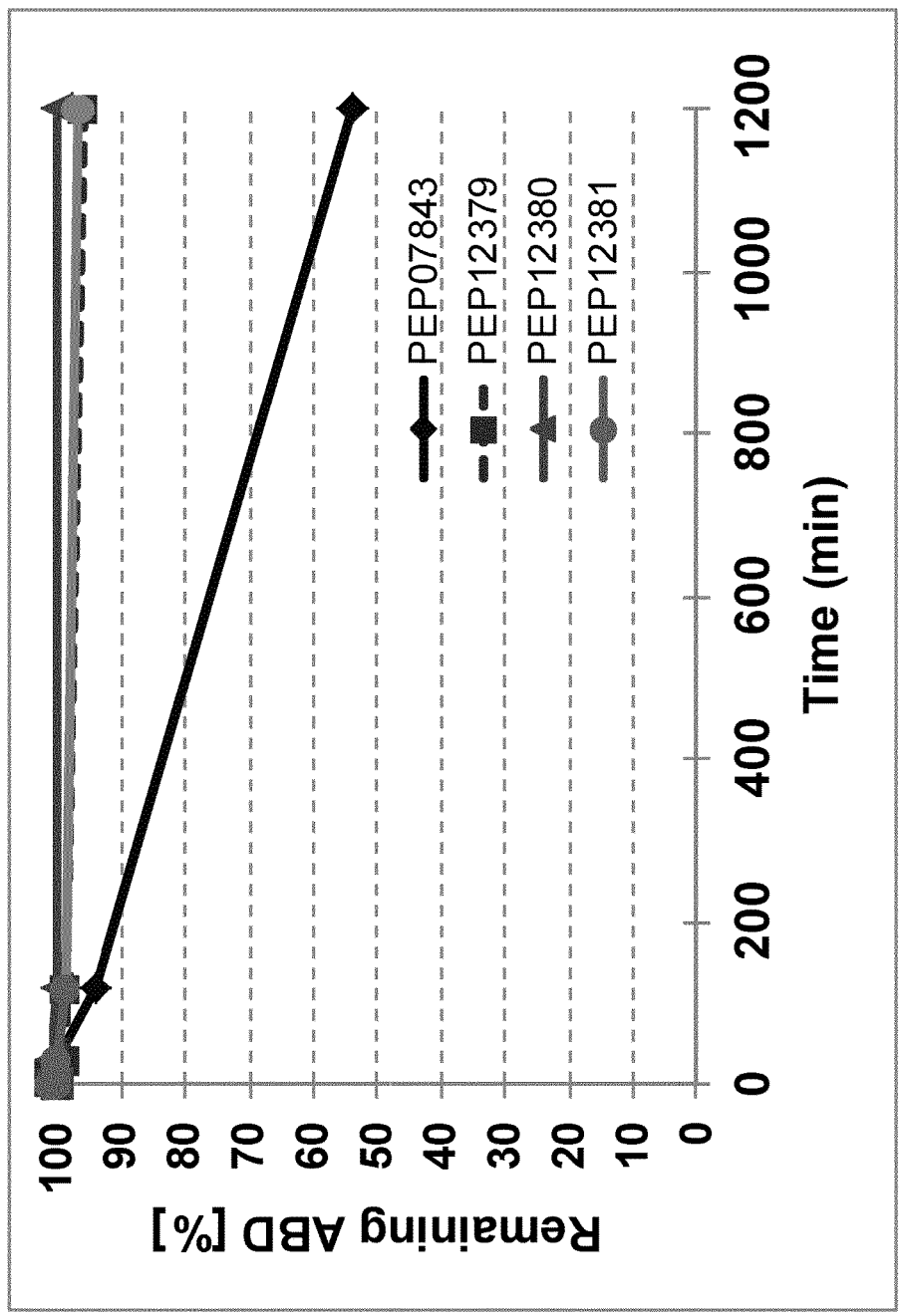
FIG. 4 shows the result of LC/MS analysis of samples of the indicated albumin binding polypeptides, incubated for up to 20 h with 0.2 U clostripain per mg polypeptide.
Figure 5:
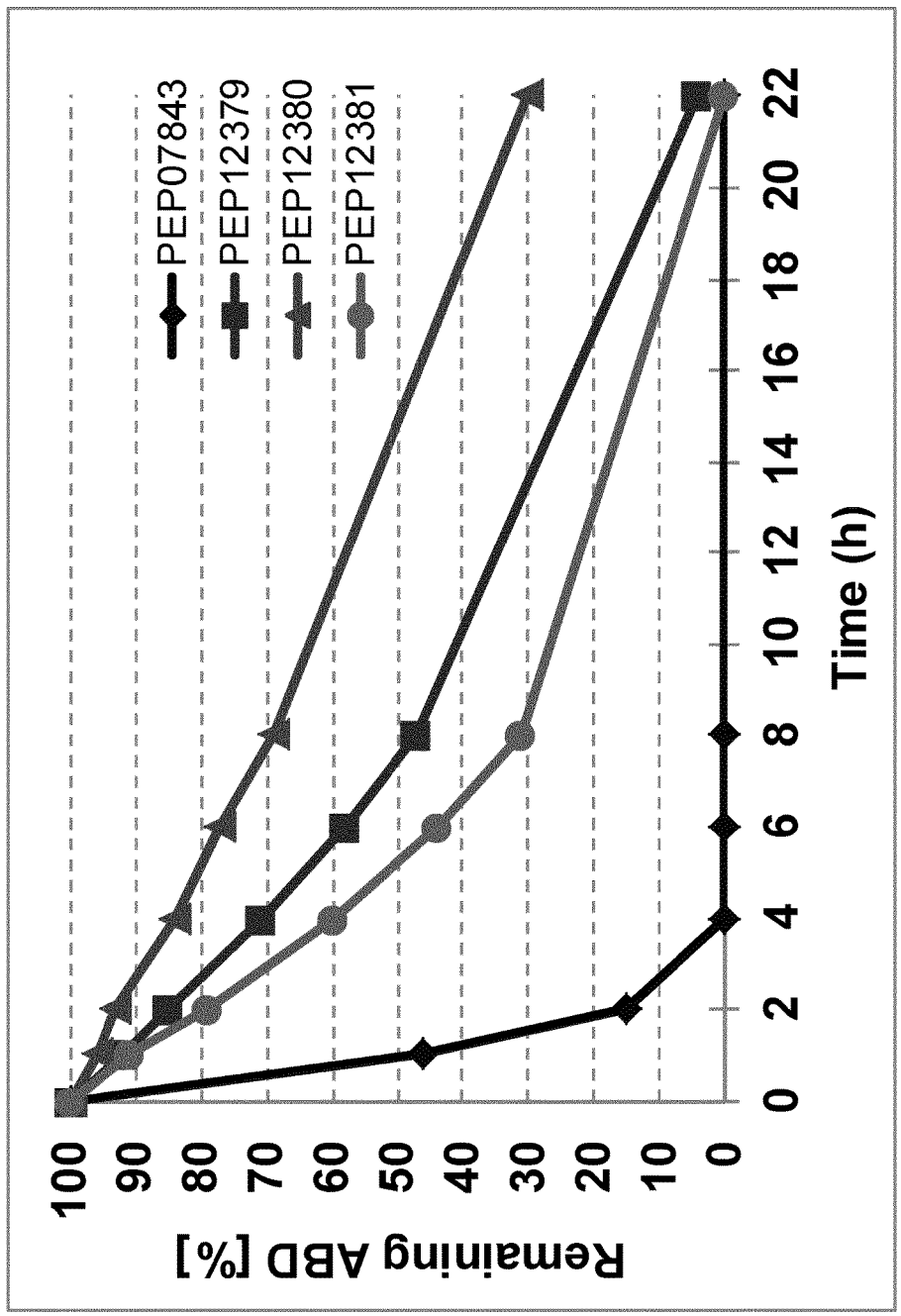
FIG. 5 shows the result of LC/MS analysis of samples of the indicated albumin binding polypeptides, incubated for up to 22 h with 5 U clostripain per mg polypeptide.

FIGS. 4 and 5 show the LC/MS analysis of ABD variant samples incubated for up to 20 h with 0.2 U and up to 22 h with 5 U respectively of clostripain per mg ABD variant. The main peak was integrated, and the area transformed to % of remaining intact ABD variant at t=0.

The results obtained are listed in Table 4 and 5 and show the remaining % ABD variant after different times of clostripain treatment. At both low and high clostripain concentrations, PEP12380 showed the lowest increase of degradation products over time, as compared to the other tested polypeptides.

TABLE 4

LC/MS analysis (0.2 U clostripain/mg ABD variant)

| Time (min) | PEP07843 | PEP12379 | PEP12380 | PEP12381 |
| --- | --- | --- | --- | --- |
| 0 | 100 | 100 | 100 | 100 |
| 2 | 100 | 100 | 100 | 101 |
| 5 | 101 | 101 | 101 | 100 |
| 15 | 100 | 101 | 101 | 100 |
| 30 | 100 | 99 | 101 | 100 |
| 120 | 94 | 99 | 100 | 99 |
| 1200 | 54 | 96 | 100 | 97 |

TABLE 5

LC/MS analysis (5 U clostripain/mg ABD variant)

| Time (h) | PEP07843 | PEP12379 | PEP12380 | PEP12381 |
| --- | --- | --- | --- | --- |
| 0 | 100 | 100 | 100 | 100 |
| 1 | 46 | 92 | 96 | 91 |
| 2 | 15 | 85 | 93 | 79 |
| 4 | 0 | 71 | 84 | 60 |
| 6 | 0 | 58 | 77 | 44 |
| 8 | 0 | 47 | 69 | 31 |
| 22 | 0 | 4 | 30 | 0 |

Figure 6:
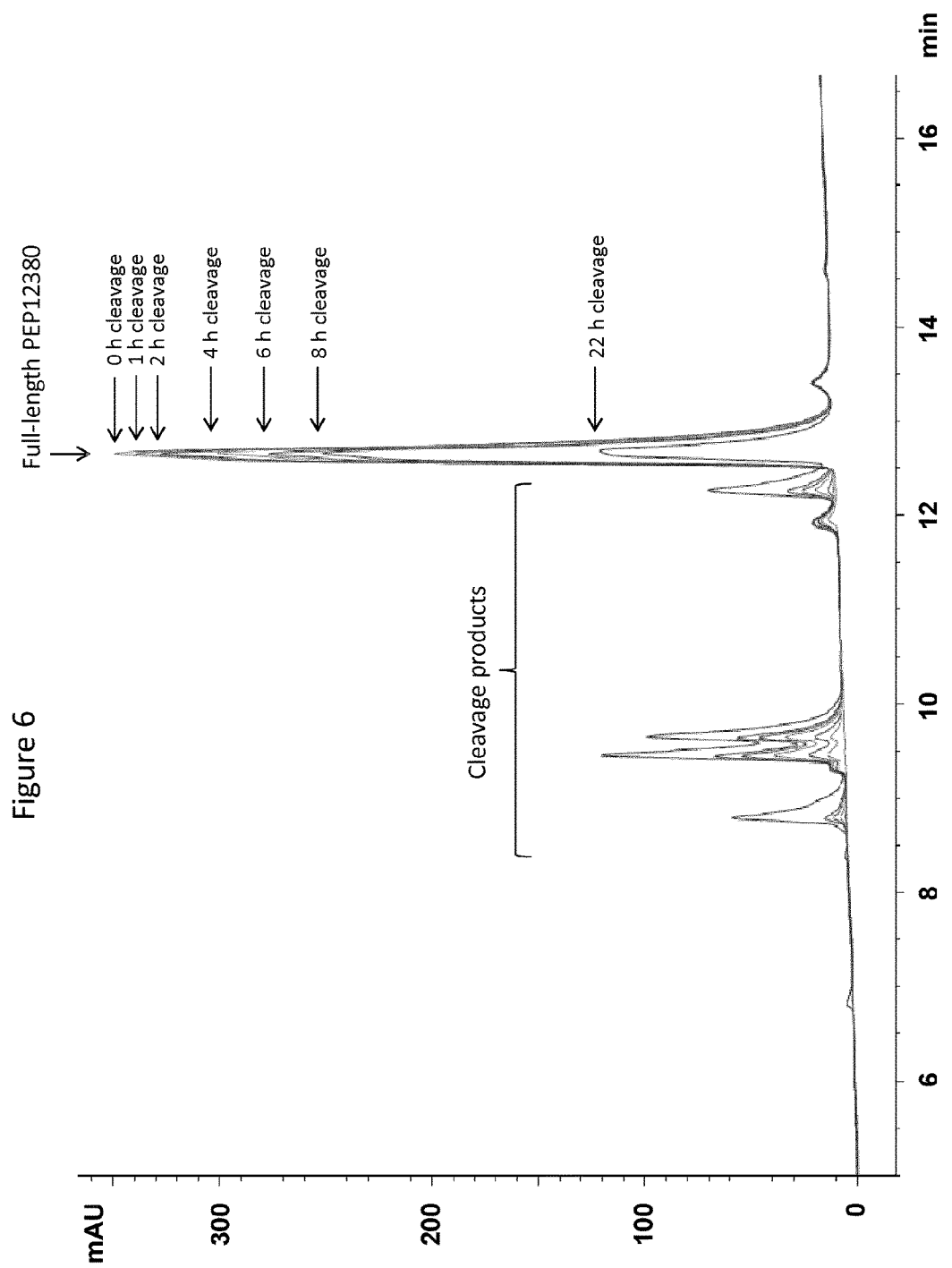
FIG. 6 shows a representative LC/MC chromatogram for samples of PEP12380 (SEQ ID NO:17), incubated for up to 22 h with 5 U clostripain per mg polypeptide.
Figure 7:
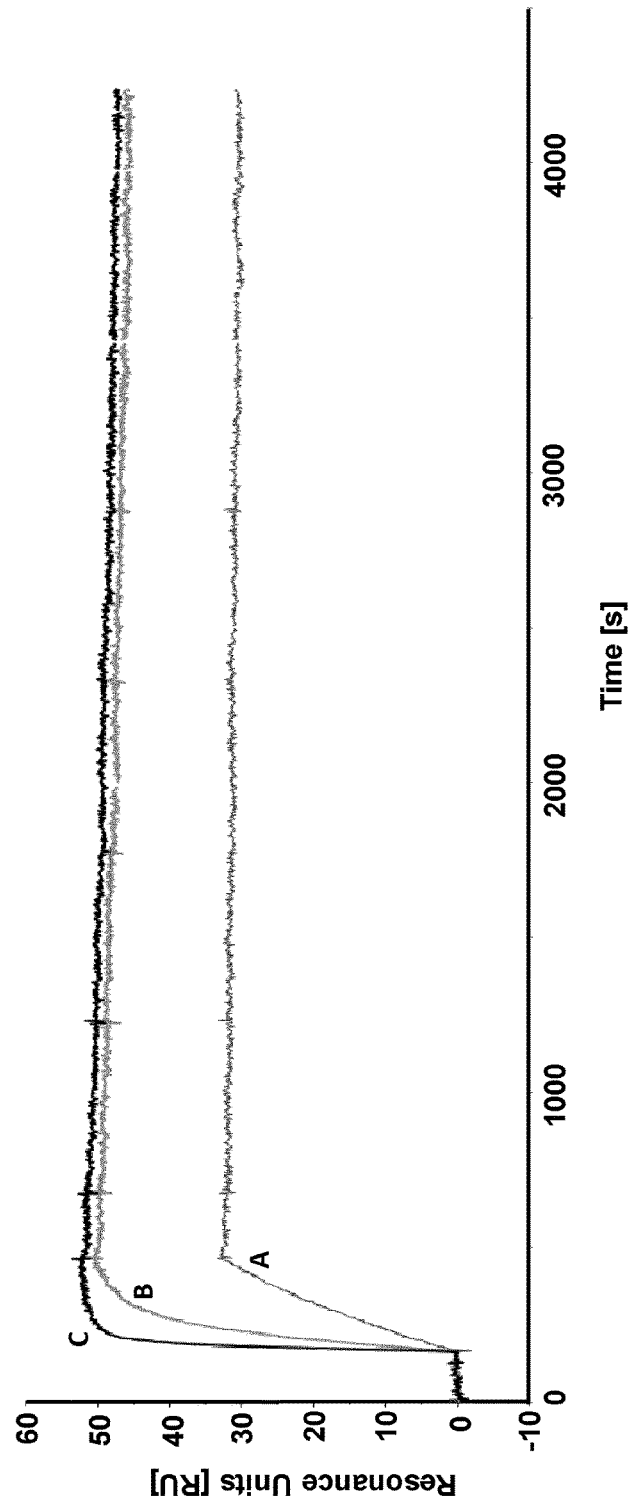
FIG. 7 shows the result of a binding analysis performed in a Biacore® instrument for investigating the binding of the indicated albumin binding polypeptide PEP12379 (SEQ ID NO:26) to human serum albumin.
Figure 8:
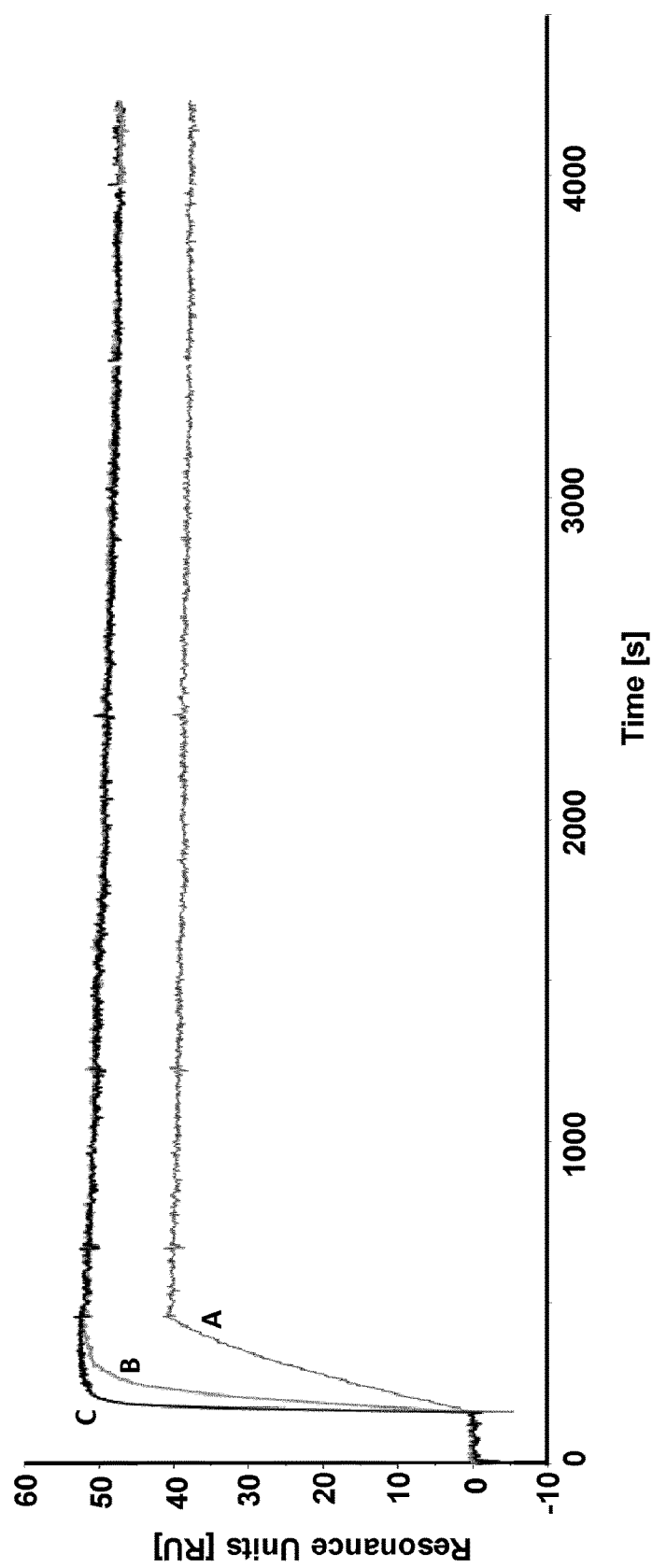
FIG. 8 shows the result of a binding analysis performed in a Biacore® instrument for investigating the binding of the indicated albumin binding polypeptide PEP12380 (SEQ ID NO:17) to human serum albumin.
Figure 9:
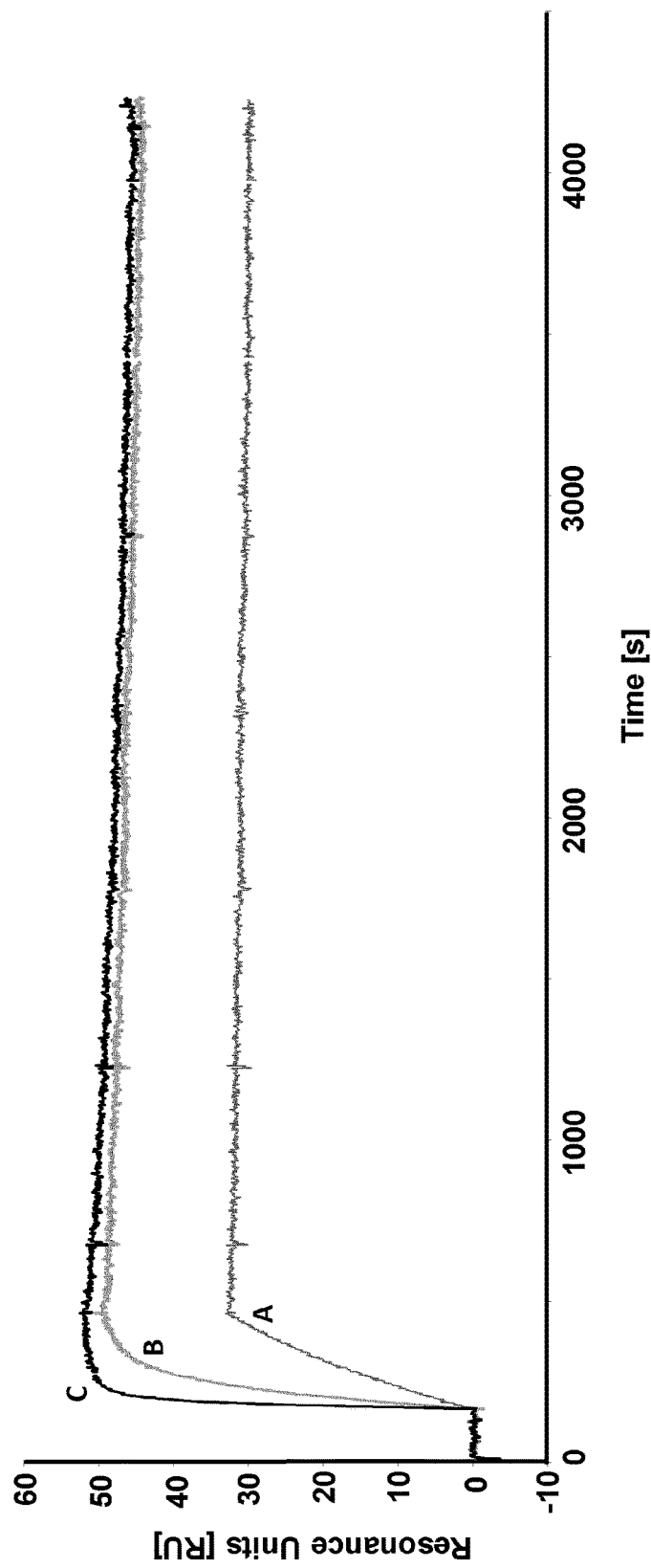
FIG. 9 shows the result of a binding analysis performed in a Biacore® instrument for investigating the binding of the indicated albumin binding polypeptide PEP12381 (SEQ ID NO:25) to human serum albumin.
Figure 10:
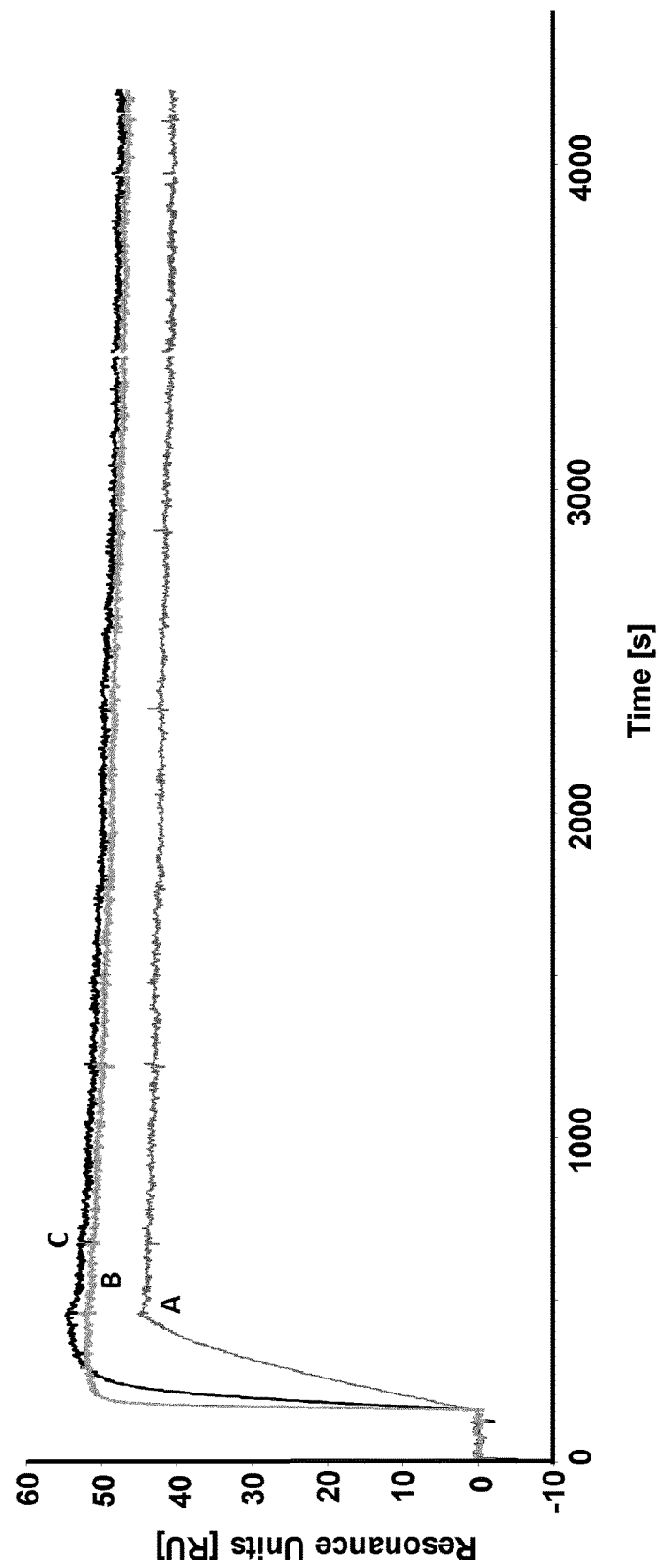
FIG. 10 shows the result of a binding analysis performed in a Biacore® instrument for investigating the binding of the indicated albumin binding polypeptide PEP07843 (SEQ ID NO:27) to human serum albumin.
Figure 11:
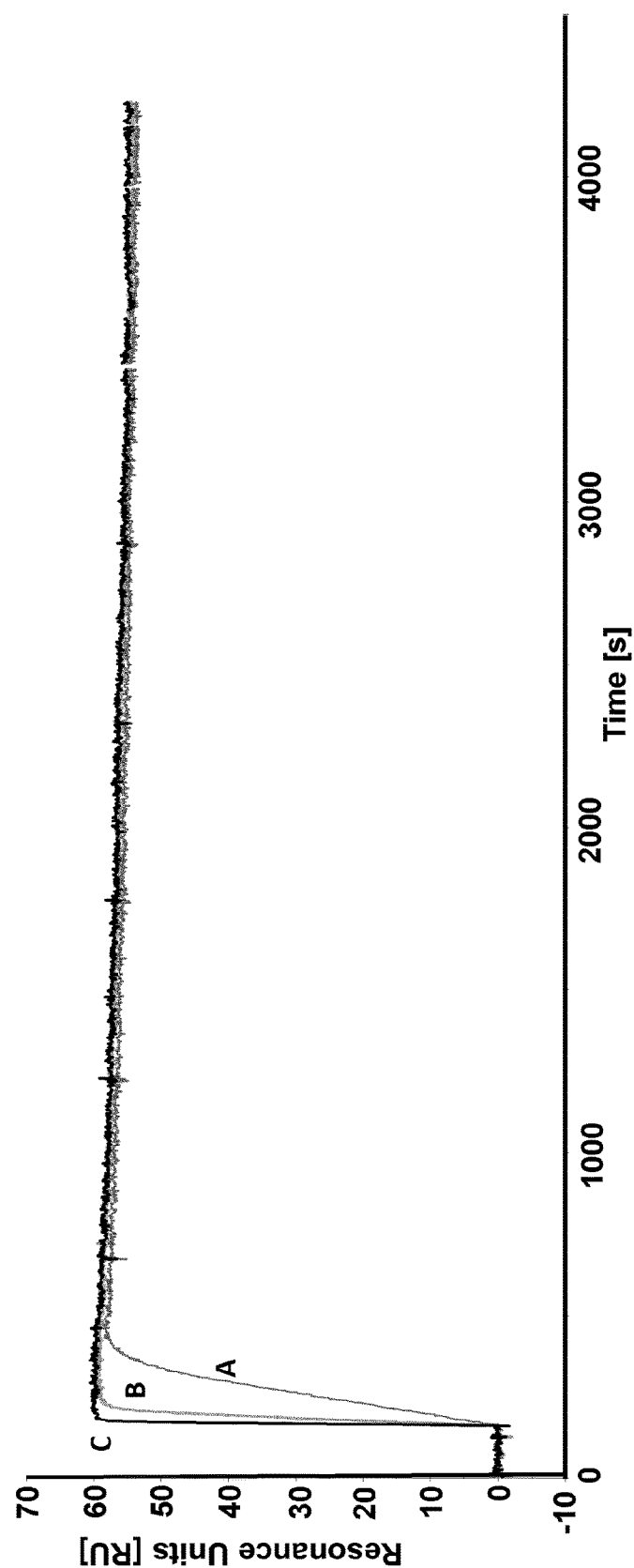
FIG. 11 shows the result of a binding analysis performed in a Biacore® instrument for investigating the binding of the indicated albumin binding polypeptide PEP06923 (SEQ ID NO:28) to human serum albumin.

FIG. 6 shows a typical LC/MS chromatogram for PEP12380 samples incubated for up to 22 h with 5 U clostripain per mg polypeptide. Similar results were obtained for the other ABD variants. The chromatogram shows the gradual decrease of full-length peptide and increase of degradation products over time.

The main peak was integrated and the area transformed to % of remaining intact ABD at t=0. The LC/MS analysis described above was used for analysis.

Example 5

Biacore Analysis

Summary

The binding of the ABD variants obtained in Example 1 to human serum albumin (HSA), rat serum albumin (RSA), cynomolgus serum albumin (CSA) and mouse serum albumin (MSA) was analyzed by surface plasmon resonance using a Biacore2000 instrument.

Materials and Methods

Biosensor analysis on a Biacore2000 instrument (GE Healthcare) was performed with HSA (Albucult®, Novozymes), CSA (purified in-house from cynomolgus serum), RSA (Sigma-Aldrich, Cat. No. A6272) and MSA (Sigma-Aldrich, Cat. No. A3559) immobilized by amine coupling onto the carboxylated dextran layer of the surfaces of CM-5 chips (research grade; GE Healthcare) according to the manufacturer's recommendations.

ABD variants were used as analytes and were injected in duplicates over the chip at three analyte concentrations (2.5, 10 and 40 nM). The association phase was 5 min followed by a long dissociation phase (60 min) to account at least partially for the slow off-rate of the ABD variants. However, due to the extremely slow off-rates of the ABD variants it was not possible to use a Biacore2000 for determination of the exact kinetic parameters including $K_D$ values. Thus, the calculated $K_D$ values can only be used for comparison in this series of experiments, and do not reflect the real $K_D$ for binding to serum albumin. Therefore, all $K_D$'s are given as relative $K_D$ values only.

The results were analyzed with BiaEvaluation software (GE Healthcare). Curves of the blank surface and buffer injection were subtracted from the curves of the ligand surfaces.

Results

The Biacore 2000 instrument has a technical limitation which hinders measurements of very high affinity. Hence, the purpose of the Biacore study was not to determine the exact kinetic parameters of the albumin binding polypeptide variants' affinity for albumin. However, the results provide a quantitative estimation of the relative affinities of these ABD variants for albumin. After subtraction of reference surface and buffer injection, curves were fitted to a 1:1 (Langmuir) binding model using BIAevaluation software with correction for mass transfer and with RUmax set as a local parameter. Sensograms of ABD variants binding to HSA are shown in FIGS. 7-11. Similar results were obtained for RSA, CSA and MSA.

A summary of the apparent kinetic parameters ($K_D$, $k_a$ ($k_{on}$) and $k_d$ ($k_{off}$)) for binding of ABD variants to HSA is given in Table 6. Similar results were obtained for RSA, CSA and MSA. Table 7 shows binding to serum albumin from different species for PEP12380 and PEP07843. Similar tendencies were obtained for the other ABD variants.

TABLE 6

Relative kinetic parameters for binding of ABD variants to HSA

| Analyte | $k_a$ (1/Ms) | $k_d$ (1/s) | $K_D$ (M) |
|---|---|---|---|
| PEP12379 | $1.70 \times 10^6$ | $2.36 \times 10^{-5}$ | $1.4 \times 10^{-11}$ |
| PEP12380 | $3.48 \times 10^6$ | $2.62 \times 10^{-5}$ | $7.5 \times 10^{-12}$ |
| PEP12381 | $1.83 \times 10^6$ | $3.08 \times 10^{-5}$ | $1.7 \times 10^{-11}$ |
| PEP07843 | $4.49 \times 10^6$ | $2.99 \times 10^{-5}$ | $6.7 \times 10^{-12}$ |
| PEP06923 | $2.81 \times 10^7$ | $2.99 \times 10^{-5}$ | $1.1 \times 10^{-12}$ |

TABLE 7

Binding of PEP12380 and PEP07843 to serum albumin from different species (relative $K_D$ values)

| Albumin species | PEP12380 $K_D$ (M) | PEP07843 $K_D$ (M) |
|---|---|---|
| HSA | $7.5 \times 10^{-12}$ | $6.7 \times 10^{-12}$ |
| RSA | $9.3 \times 10^{-12}$ | $8.2 \times 10^{-12}$ |
| CSA | $1.1 \times 10^{-11}$ | $9.8 \times 10^{-12}$ |
| MSA | $1.17 \times 10^{-10}$ | $8.7 \times 10^{-11}$ |

In conclusion, the PEP12380 variant exhibits similar albumin binding characteristics, as judged by the kinetic parameters above, as the PEP07843 variant, while variants PEP12379 and PEP12381 exhibit lower binding affinities to albumin. Importantly PEP12380 exhibits superior properties with respect to protease stability as compared to all of PEP12379, PEP12381 and PEP07843.

Itemized Listing of Embodiments

1. Albumin binding polypeptide comprising an albumin binding motif [BM], which motif consists of the amino acid sequence:

GVSDFYKKLI X$_a$KAKTVEGVE ALKX$_b$X$_c$I (SEQ ID NO:29)

wherein, independently of each other,
   X$_a$ is selected from D and E;
   X$_b$ is selected from D and E; and
   X$_c$ is selected from A and E.
2. Albumin binding polypeptide according to item 1, wherein X$_a$ is D.
3. Albumin binding polypeptide according to any preceding item, wherein X$_b$ is D.
4. Albumin binding polypeptide according to any preceding item, wherein X, is A.
5. Albumin binding polypeptide according to item 1, wherein the sequence is SEQ ID NO:1.
6. Albumin binding polypeptide according to any preceding item, wherein said albumin binding motif forms part of a three-helix bundle protein domain.
7. Albumin binding polypeptide according to item 6, wherein said three-helix bundle protein domain is selected from the group consisting of three-helix domains of bacterial receptor proteins.
8. Albumin binding polypeptide according to item 7, wherein said bacterial receptor protein is selected from the group consisting of albumin binding receptor proteins from species of *Streptococcus, Peptostreptococcus* and *Finegoldia*.
9. Albumin binding polypeptide according to item 8, wherein said albumin binding receptor protein is selected from the group consisting of protein G; MAG; ZAG; PPL; and PAB.
10. Albumin binding polypeptide according to item 9, wherein said albumin binding receptor protein is protein G.
11. Albumin binding polypeptide according to item 10, wherein said albumin binding receptor protein is protein G from *Streptococcus* strain G148.
12. Albumin binding polypeptide according to item 11, wherein said three-helix bundle protein domain is selected from the group consisting of domain GA1, domain GA2 and domain GA3 of protein G from *Streptococcus* strain G148.

13. Albumin binding polypeptide according to item 12, wherein said three-helix bundle protein domain is domain GA3 of protein G from *Streptococcus* strain G148.
14. Albumin binding polypeptide according to item 6, which comprises the amino acid sequence:

LAX$_3$AKX$_6$X$_7$ANX$_{10}$ ELDX$_{14}$Y-[BM]-LX$_{43}$ X$_{44}$LP (SEQ ID NO:30)

wherein
[BM] is an albumin binding motif as defined in any one of items 1-5,
and, independently of each other,
X$_3$ is selected from C, E, Q and S;
X$_6$ is selected from C, E and S;
X$_7$ is selected from A and S;
X$_{10}$ is selected from A, R and S;
X$_{14}$ is selected from A, C, K and S;
X$_{43}$ is selected from A and K; and
X$_{44}$ is selected from A, E and S.
15. Albumin binding polypeptide according to item 14, wherein X$_3$ is E.
16. Albumin binding polypeptide according to any one of items 14-15, wherein X$_6$ is E.
17. Albumin binding polypeptide according to any one of items 14-16, wherein X$_7$ is A.
18. Albumin binding polypeptide according to any one of items 14-17, wherein X$_{10}$ is A.
19. Albumin binding polypeptide according to any one of items 14-18, wherein X$_{14}$ is S.
20. Albumin binding polypeptide according to any one of items 14-19, wherein X$_{43}$ is A.
21. Albumin binding polypeptide according to any one of items 14-20, wherein X$_{44}$ is A.
22. Albumin binding polypeptide, whose amino acid sequence comprises a sequence which fulfils one definition selected from the following:
    i) it is selected from SEQ ID NO:9-16;
    ii) it is an amino acid sequence having 93% or greater identity to a sequence selected from SEQ ID NO: 9-16 provided that the amino acid in the position corresponding to position 23 in SEQ ID NO:9-16 is K.
23. Albumin binding polypeptide according to item 22, whose amino acid sequence comprises a sequence which fulfils one definition selected from the following:
    iii) it is SEQ ID NO:9;
    iv) it is an amino acid sequence having 93% or greater identity to SEQ ID NO:9 provided that the amino acid in the position corresponding to position 23 in SEQ ID NO:9 is K.
24. Albumin binding polypeptide according to any one of items 14-23, which additionally comprises at least one serine residue at the N-terminal side of the polypeptide sequence as defined in any one of items 14-23.
25. Albumin binding polypeptide according to any one of items 14-24, which additionally comprises a glycine residue at the N-terminal side of the polypeptide sequence as defined in any one of items 14-24.
26. Albumin binding polypeptide according to any one of items 24 and 25, which additionally comprises the amino acids GSS at the N-terminal side of the polypeptide sequence as defined in any one of items 14-25.
27. Albumin binding polypeptide according to item 26, whose amino acid sequence is selected from SEQ ID NO:17-24.
28. Albumin binding polypeptide according to item 27, whose amino acid sequence is SEQ ID NO:17.
29. Albumin binding polypeptide according to any one of items 14-28, which additionally comprises a cysteine residue at the N-terminal side of the polypeptide sequence as defined in any one of items 14-28.
30. Albumin binding polypeptide according to any one of items 14-29, which additionally comprises a lysine residue at the C-terminal side of the polypeptide sequence as defined in any one of items 14-29.
31. Albumin binding polypeptide according to any one of items 14-30, which additionally comprises a glycine residue at the C-terminal side of the polypeptide sequence as defined in any one of the items 14-30.
32. Albumin binding polypeptide according to any one of items 14-31, which additionally comprises a cysteine residue at the C-terminal side of the polypeptide sequence as defined in any one of items 14-31.
33. Albumin binding polypeptide according to any preceding item, comprising no more than two cysteine residues.
34. Albumin binding polypeptide according to item 33, comprising no more than one cysteine residue.
35. Albumin binding polypeptide according to any preceding item, wherein the albumin binding polypeptide binds to albumin such that the K$_D$ value of the interaction is at most $1 \times 10^{-9}$ M, such as at most $1 \times 10^{-10}$ M, such as at most $1 \times 10^{-11}$ M, such as at most $1 \times 10^{-12}$ M, such as at most $1 \times 10^{-13}$ M, such as at most $1 \times 10^{-14}$ M.
36. Fusion protein or conjugate comprising
    i) a first moiety consisting of an albumin binding polypeptide according to any preceding item; and
    ii) a second moiety consisting of a polypeptide having a desired biological activity.
37. Fusion protein or conjugate according to item 36, wherein said desired biological activity is a therapeutic activity.
38. Fusion protein or conjugate according to item 36, wherein said desired biological activity is a binding activity.
39. Fusion protein or conjugate according to item 36, wherein said desired biological activity is an enzymatic activity.
40. Fusion protein or conjugate according to item 37, wherein the second moiety having a desired biological activity is a therapeutically active polypeptide.
41. Fusion protein or conjugate according to item 36, wherein the second moiety having a desired biological activity is selected from the group consisting of human endogenous enzymes, hormones, growth factors, chemokines, cytokines and lymphokines.
42. Fusion protein or conjugate according to item 41, wherein the second moiety is selected from the group consisting of IL-2, GLP-1, BNP, IL-1 receptor agonist, KGF, Stemgen®, GH, G-CSF, CTLA-4, myostatin, Factor VII, Factor VIII, Factor IX and Factor X.
43. Fusion protein or conjugate according to item 36, wherein the second moiety having a desired biological activity is a non-human biologically active protein, selected from the group consisting of bacterial toxins, enzymes and activating proteins.
44. Fusion protein or conjugate according to item 36, wherein the second moiety having a desired biological activity is a binding polypeptide capable of selective interaction with a target molecule.
45. Fusion protein or conjugate according to item 44, wherein the binding polypeptide is selected from the group consisting of antibodies and fragments and domains thereof substantially retaining antibody binding activity; microbodies, maxybodies, avimers and other small disulfide-bonded proteins; and binding proteins derived from a scaffold selected from the group consisting of staphylococcal protein A and domains thereof, other three helix domains, lipocalins, ankyrin repeat domains, cellulose binding domains, γ crystallines, green fluorescent protein, human cytotoxic T lymphocyte-associated antigen 4, protease inhibitors such as Kunitz domains, PDZ domains, SH3 domains, peptide aptamers, staphylococcal nuclease, tendamistats, fibronectin type III domain, transferrin, zinc fingers and conotoxins.

46. Fusion protein or conjugate according to any one of items 44 and 45, wherein said target molecule is selected from the group consisting of Aβ peptide of Alzheimer's disease; other disease-associated amyloid peptides; toxins, such as bacterial toxins and snake venoms; blood clotting factors, such as von Willebrand factor; interleukins, such as IL-13; myostatin; pro-inflammatory factors, such as TNF-α, TNF-α receptor, IL-1, IL-23 and IL-8; complement factors, such as C3 and C5; hypersensitivity mediators, such as histamine and IgE; tumor-related antigens, such as CD19, CD20, CD22, CD30, CD33, CD40, CD52, CD70, cMet, HER1, HER2, HER3, HER4, CAIX, CEA, IL-2 receptor, MUC1, PSMA, TAG-72, and other biological molecules such as G-CSF, GM-CSF, GH, insulin and somatostatin.

47. Fusion protein or conjugate according to any one of items 36-46, comprising a further moiety consisting of a polypeptide having a further, desired biological activity, which may be the same as or different from that of the second moiety.

48. Fusion protein or conjugate according to item 47, wherein the second moiety is as defined in any one of items 40-43, and the further moiety is as defined in any one of items 44-46.

49. Fusion protein or conjugate according to item 47, wherein the second moiety and the further moiety each individually is as defined in any one of items 44-46.

50. Conjugate according to any one of items 36-49, wherein the second moiety is conjugated to a first moiety according to any one of items 1-35 via the thiol group of any cysteine residue present, for example at position $X_{14}$ of a first moiety as defined in any one of items 14-35.

51. Albumin binding polypeptide, fusion protein or conjugate according to any preceding item, further comprising a cytotoxic agent.

52. Albumin binding polypeptide, fusion protein or conjugate according to item 51, wherein the cytotoxic agent is selected from calicheamycin, auristatin, doxorubicin, maytansinoid, taxol, ecteinascidin, geldanamycin, methotrexate and their derivatives, and combinations thereof.

53. Albumin binding polypeptide, fusion protein or conjugate according to any preceding item further comprising a label.

54. Albumin binding polypeptide, fusion protein or conjugate according to item 53, wherein said label is selected from the group consisting of fluorescent dyes and metals, chromophoric dyes, chemiluminescent compounds and bioluminescent proteins, enzymes, radionuclides and particles.

55. Albumin binding polypeptide, fusion protein or conjugate according to item 54, comprising a chelating environment provided by a polyaminopolycarboxylate chelator conjugated to the albumin binding polypeptide via a thiol group of a cysteine residue or an amine group of a lysine residue.

56. Albumin binding polypeptide, fusion protein or conjugate according to item 55, wherein the polyaminopolycarboxylate chelator is 1,4,7,10-tetraazacyclododecane-1,4,7,10-tetraacetic acid or a derivative thereof.

57. Albumin binding polypeptide, fusion protein or conjugate according to item 56, wherein the 1,4,7,10-tetraazacyclododecane-1,4,7,10-tetraacetic acid derivative is 1,4,7,10-tetraazacyclododecane-1,4,7-tris-acetic acid-10-maleimidoethylacetamide.

58. Albumin binding polypeptide, fusion protein or conjugate according to item 55, wherein the the polyaminopolycarboxylate chelator is 1,4,7-triazacyclononane-1,4,7-triacetic acid or a derivative thereof.

59. Albumin binding polypeptide, fusion protein or conjugate according to item 55, wherein the polyaminopolycarboxylate chelator is diethylenetriaminepentaacetic acid or derivatives thereof.

60. Polynucleotide encoding an albumin binding polypeptide or a fusion protein according to any one of items 1-49.

61. Method of producing a polypeptide according to any one of items 1-49, comprising expressing a polynucleotide according to item 60.

62. Expression vector comprising a polynucleotide according to item 60.

63. Host cell comprising an expression vector according to item 62.

64. Method of producing a polypeptide according to any one of items 1-49, comprising
   i) culturing a host cell according to item 63 under conditions permitting expression of said polypeptide from said expression vector, and
   ii) isolating the polypeptide.

The invention claimed is:

1. An albumin binding polypeptide comprising an albumin binding motif [BM], which motif consists of the amino acid sequence:

(SEQ ID NO: 29)
GVSDFYKKLI X$_a$KAKTVEGVE ALKX$_b$X$_c$I wherein, independently of each other,
X$_a$ is selected from D and E;
X$_b$ is selected from D and E; and
Xc is selected from A and E,
wherein the albumin binding motif has enhanced resistance to clostripain cleavage compared to the motif of SEQ ID NO:29 with position 8 substituted with R, S, or N.

2. The albumin binding polypeptide according to claim 1, wherein the sequence is SEQ ID NO:1.

3. The albumin binding polypeptide according to claim 1, wherein said albumin binding motif forms part of a three-helix bundle protein domain.

4. The albumin binding polypeptide according to claim 3, which comprises the amino acid sequence:

(SEQ ID NO: 30)
LAX$_3$AKX$_6$X$_7$ANX$_{10}$ ELDX$_{14}$Y-[BM]-LX$_{43}$X$_{44}$LP wherein
[BM] is an albumin binding motif as defined in claim 1,
and, independently of each other,
X$_3$ is selected from C, E, Q and S;
X$_6$ is selected from C, E and S;
X$_7$ is selected from A and S;
X$_{10}$ is selected from A and S;
X$_{14}$ is selected from A, C, K and S;
X$_{43}$ is selected from A and K; and
X$_{44}$ is selected from A, E and S.

5. The albumin binding polypeptide according to claim 4, wherein the albumin binding polypeptide comprises the amino acid sequence of
SEQ ID NO:9, 10, 11, 12, 13, 14, 15, or 16.

6. The albumin binding polypeptide according to claim 5, wherein the albumin binding polypeptide comprises the amino acid sequence of SEQ ID NO:17, 18, 19, 20, 21, 22, 23, or 24.

7. The albumin binding polypeptide according to claim 1, wherein the albumin binding polypeptide binds to albumin such that the K$_D$ value of the interaction is at most $1 \times 10^{-9}$ M.

8. The albumin binding polypeptide of claim 1, further comprising a label.

9. The albumin binding polypeptide according to claim 8, wherein said label is selected from the group consisting of fluorescent dyes and metals, chromophoric dyes, chemiluminescent compounds, bioluminescent proteins, enzymes, radionuclides and particles.

10. The albumin binding polypeptide according to claim 5, wherein the amino acid sequence is SEQ ID NO:17.

11. The albumin binding polypeptide according to claim 1, wherein the albumin binding polypeptide binds to albumin such that the K$_D$ value of the interaction is at most $1 \times 10^{-10}$ M.

12. The albumin binding polypeptide according to claim 1, wherein the albumin binding polypeptide binds to albumin such that the $K_D$ value of the interaction is at most $1 \times 10^{-11}$ M.

13. The albumin binding polypeptide according to claim 1, wherein the albumin binding polypeptide binds to albumin such that the $K_D$ value of the interaction is at most $1 \times 10^{-12}$ M.

14. The albumin binding polypeptide according to claim 1, wherein the albumin binding polypeptide binds to albumin such that the $K_D$ value of the interaction is at most $1 \times 10^{-13}$ M.

15. The albumin binding polypeptide according to claim 1, wherein the albumin binding polypeptide binds to albumin such that the $K_D$ value of the interaction is at most $1 \times 10^{-14}$ M.

16. A fusion protein or conjugate comprising
   i) a first moiety consisting of an albumin binding polypeptide according to claim 1; and
   ii) a second moiety consisting of a polypeptide having a desired biological activity.

17. The fusion protein or conjugate according to claim 16, wherein the second moiety having a desired biological activity is a therapeutically active polypeptide.

18. The fusion protein or conjugate according to claim 16, wherein the second moiety having a desired biological activity is a binding polypeptide capable of selective interaction with a target molecule.

19. The fusion protein or conjugate of claim 16, further comprising a label.

20. The fusion protein or conjugate of claim 19, wherein said label is selected from the group consisting of fluorescent dyes and metals, chromophoric dyes, chemiluminescent compounds, bioluminescent proteins, enzymes, radionuclides and particles.

21. A polynucleotide encoding an albumin binding polypeptide according to claim 1.

22. A polynucleotide encoding a fusion protein or conjugate according to claim 16.

23. A method of producing a polypeptide according to claim 1, comprising expressing a polynucleotide according to claim 21.

24. A method of producing the fusion protein or conjugate according to claim 16, comprising expressing a polynucleotide according to claim 22.

* * * * *

SEQUENCE LISTING

<160> NUMBER OF SEQ ID NOS: 30

<210> SEQ ID NO 1
<211> LENGTH: 26
<212> TYPE: PRT
<213> ORGANISM: Artificial
<220> FEATURE:
<223> OTHER INFORMATION: Engineered albumin binding polypeptide

<400> SEQUENCE: 1

Gly Val Ser Asp Phe Tyr Lys Lys Leu Ile Asp Lys Ala Lys Thr Val
1               5                   10                  15

Glu Gly Val Glu Ala Leu Lys Asp Ala Ile
            20                  25

```
<210> SEQ ID NO 2
<211> LENGTH: 26
<212> TYPE: PRT
<213> ORGANISM: Artificial
<220> FEATURE:
<223> OTHER INFORMATION: Engineered albumin binding polypeptide

<400> SEQUENCE: 2

Gly Val Ser Asp Phe Tyr Lys Lys Leu Ile Asp Lys Ala Lys Thr Val
1               5                   10                  15

Glu Gly Val Glu Ala Leu Lys Asp Glu Ile
            20                  25

<210> SEQ ID NO 3
<211> LENGTH: 26
<212> TYPE: PRT
<213> ORGANISM: Artificial
<220> FEATURE:
<223> OTHER INFORMATION: Engineered albumin binding polypeptide

<400> SEQUENCE: 3

Gly Val Ser Asp Phe Tyr Lys Lys Leu Ile Asp Lys Ala Lys Thr Val
1               5                   10                  15

Glu Gly Val Glu Ala Leu Lys Glu Ala Ile
            20                  25

<210> SEQ ID NO 4
<211> LENGTH: 26
<212> TYPE: PRT
<213> ORGANISM: Artificial
<220> FEATURE:
<223> OTHER INFORMATION: Engineered albumin binding polypeptide

<400> SEQUENCE: 4

Gly Val Ser Asp Phe Tyr Lys Lys Leu Ile Asp Lys Ala Lys Thr Val
1               5                   10                  15

Glu Gly Val Glu Ala Leu Lys Glu Glu Ile
            20                  25

<210> SEQ ID NO 5
<211> LENGTH: 26
<212> TYPE: PRT
<213> ORGANISM: Artificial
<220> FEATURE:
<223> OTHER INFORMATION: Engineered albumin binding polypeptide

<400> SEQUENCE: 5

Gly Val Ser Asp Phe Tyr Lys Lys Leu Ile Glu Lys Ala Lys Thr Val
1               5                   10                  15

Glu Gly Val Glu Ala Leu Lys Asp Ala Ile
            20                  25

<210> SEQ ID NO 6
<211> LENGTH: 26
<212> TYPE: PRT
<213> ORGANISM: Artificial
<220> FEATURE:
<223> OTHER INFORMATION: Engineered albumin binding polypeptide

<400> SEQUENCE: 6

Gly Val Ser Asp Phe Tyr Lys Lys Leu Ile Glu Lys Ala Lys Thr Val
1               5                   10                  15

Glu Gly Val Glu Ala Leu Lys Asp Glu Ile
```

20                  25

<210> SEQ ID NO 7
<211> LENGTH: 26
<212> TYPE: PRT
<213> ORGANISM: Artificial
<220> FEATURE:
<223> OTHER INFORMATION: Engineered albumin binding polypeptide

<400> SEQUENCE: 7

Gly Val Ser Asp Phe Tyr Lys Lys Leu Ile Glu Lys Ala Lys Thr Val
1               5                   10                  15

Glu Gly Val Glu Ala Leu Lys Glu Ala Ile
            20                  25

<210> SEQ ID NO 8
<211> LENGTH: 26
<212> TYPE: PRT
<213> ORGANISM: Artificial
<220> FEATURE:
<223> OTHER INFORMATION: Engineered albumin binding polypeptide

<400> SEQUENCE: 8

Gly Val Ser Asp Phe Tyr Lys Lys Leu Ile Glu Lys Ala Lys Thr Val
1               5                   10                  15

Glu Gly Val Glu Ala Leu Lys Glu Glu Ile
            20                  25

<210> SEQ ID NO 9
<211> LENGTH: 46
<212> TYPE: PRT
<213> ORGANISM: Artificial
<220> FEATURE:
<223> OTHER INFORMATION: Engineered albumin binding polypeptide

<400> SEQUENCE: 9

Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 10
<211> LENGTH: 46
<212> TYPE: PRT
<213> ORGANISM: Artificial
<220> FEATURE:
<223> OTHER INFORMATION: Engineered albumin binding polypeptide

<400> SEQUENCE: 10

Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
            20                  25                  30

Gly Val Glu Ala Leu Lys Asp Glu Ile Leu Ala Ala Leu Pro
        35                  40                  45

<210> SEQ ID NO 11
<211> LENGTH: 46
<212> TYPE: PRT
<213> ORGANISM: Artificial
<220> FEATURE:
<223> OTHER INFORMATION: Engineered albumin binding polypeptide

```
<400> SEQUENCE: 11

Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 12
<211> LENGTH: 46
<212> TYPE: PRT
<213> ORGANISM: Artificial
<220> FEATURE:
<223> OTHER INFORMATION: Engineered albumin binding polypeptide

<400> SEQUENCE: 12

Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
            20                  25                  30

Gly Val Glu Ala Leu Lys Glu Glu Ile Leu Ala Ala Leu Pro
        35                  40                  45

<210> SEQ ID NO 13
<211> LENGTH: 46
<212> TYPE: PRT
<213> ORGANISM: Artificial
<220> FEATURE:
<223> OTHER INFORMATION: Engineered albumin binding polypeptide

<400> SEQUENCE: 13

Leu Ala Glu Ala Lys Glu Ala Ala Asn Ala Glu Leu Asp Ser Tyr Gly
1               5                   10                  15

Val Ser Asp Phe Tyr Lys Lys Leu Ile Glu Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 14
<211> LENGTH: 46
<212> TYPE: PRT
<213> ORGANISM: Artificial
<220> FEATURE:
<223> OTHER INFORMATION: Engineered albumin binding polypeptide

<400> SEQUENCE: 14

Leu Ala Glu Ala Lys Glu Ala Ala Asn Ala Glu Leu Asp Ser Tyr Gly
1               5                   10                  15

Val Ser Asp Phe Tyr Lys Lys Leu Ile Glu Lys Ala Lys Thr Val Glu
            20                  25                  30

Gly Val Glu Ala Leu Lys Asp Glu Ile Leu Ala Ala Leu Pro
        35                  40                  45

<210> SEQ ID NO 15
<211> LENGTH: 46
<212> TYPE: PRT
<213> ORGANISM: Artificial
<220> FEATURE:
<223> OTHER INFORMATION: Engineered albumin binding polypeptide

<400> SEQUENCE: 15
```

```
Leu Ala Glu Ala Lys Glu Ala Asn Ala Glu Leu Asp Ser Tyr Gly
1               5                   10                  15

Val Ser Asp Phe Tyr Lys Lys Leu Ile Glu Lys Ala Lys Thr Val Glu
            20                  25                  30

Gly Val Glu Ala Leu Lys Glu Ala Ile Leu Ala Ala Leu Pro
        35                  40                  45
```

<210> SEQ ID NO 16
<211> LENGTH: 46
<212> TYPE: PRT
<213> ORGANISM: Artificial
<220> FEATURE:
<223> OTHER INFORMATION: Engineered albumin binding polypeptide

<400> SEQUENCE: 16

```
Leu Ala Glu Ala Lys Glu Ala Asn Ala Glu Leu Asp Ser Tyr Gly
1               5                   10                  15

Val Ser Asp Phe Tyr Lys Lys Leu Ile Glu Lys Ala Lys Thr Val Glu
            20                  25                  30

Gly Val Glu Ala Leu Lys Glu Glu Ile Leu Ala Ala Leu Pro
        35                  40                  45
```

<210> SEQ ID NO 17
<211> LENGTH: 49
<212> TYPE: PRT
<213> ORGANISM: Artificial
<220> FEATURE:
<223> OTHER INFORMATION: Engineered albumin binding polypeptide

<400> SEQUENCE: 17

```
Gly Ser Ser Leu Ala Glu Ala Lys Glu Ala Ala Asn Ala Glu Leu Asp
1               5                   10                  15

Ser Tyr Gly Val Ser Asp Phe Tyr Lys Lys Leu Ile Asp Lys Ala Lys
            20                  25                  30

Thr Val Glu Gly Val Glu Ala Leu Lys Asp Ala Ile Leu Ala Ala Leu
        35                  40                  45

Pro
```

<210> SEQ ID NO 18
<211> LENGTH: 49
<212> TYPE: PRT
<213> ORGANISM: Artificial
<220> FEATURE:
<223> OTHER INFORMATION: Engineered albumin binding polypeptide

<400> SEQUENCE: 18

```
Gly Ser Ser Leu Ala Glu Ala Lys Glu Ala Ala Asn Ala Glu Leu Asp
1               5                   10                  15

Ser Tyr Gly Val Ser Asp Phe Tyr Lys Lys Leu Ile Asp Lys Ala Lys
            20                  25                  30

Thr Val Glu Gly Val Glu Ala Leu Lys Asp Glu Ile Leu Ala Ala Leu
        35                  40                  45

Pro
```

<210> SEQ ID NO 19
<211> LENGTH: 49
<212> TYPE: PRT
<213> ORGANISM: Artificial
<220> FEATURE:
<223> OTHER INFORMATION: Engineered albumin binding polypeptide

<400> SEQUENCE: 19

Gly Ser Ser Leu Ala Glu Ala Lys Glu Ala Ala Asn Ala Glu Leu Asp
1               5                   10                  15

Ser Tyr Gly Val Ser Asp Phe Tyr Lys Lys Leu Ile Asp Lys Ala Lys
            20                  25                  30

Thr Val Glu Gly Val Glu Ala Leu Lys Glu Ala Ile Leu Ala Ala Leu
        35                  40                  45

Pro

<210> SEQ ID NO 20
<211> LENGTH: 49
<212> TYPE: PRT
<213> ORGANISM: Artificial
<220> FEATURE:
<223> OTHER INFORMATION: Engineered albumin binding polypeptide

<400> SEQUENCE: 20

Gly Ser Ser Leu Ala Glu Ala Lys Glu Ala Ala Asn Ala Glu Leu Asp
1               5                   10                  15

Ser Tyr Gly Val Ser Asp Phe Tyr Lys Lys Leu Ile Asp Lys Ala Lys
            20                  25                  30

Thr Val Glu Gly Val Glu Ala Leu Lys Glu Glu Ile Leu Ala Ala Leu
        35                  40                  45

Pro

<210> SEQ ID NO 21
<211> LENGTH: 49
<212> TYPE: PRT
<213> ORGANISM: Artificial
<220> FEATURE:
<223> OTHER INFORMATION: Engineered albumin binding polypeptide

<400> SEQUENCE: 21

Gly Ser Ser Leu Ala Glu Ala Lys Glu Ala Ala Asn Ala Glu Leu Asp
1               5                   10                  15

Ser Tyr Gly Val Ser Asp Phe Tyr Lys Lys Leu Ile Glu Lys Ala Lys
            20                  25                  30

Thr Val Glu Gly Val Glu Ala Leu Lys Asp Ala Ile Leu Ala Ala Leu
        35                  40                  45

Pro

<210> SEQ ID NO 22
<211> LENGTH: 49
<212> TYPE: PRT
<213> ORGANISM: Artificial
<220> FEATURE:
<223> OTHER INFORMATION: Engineered albumin binding polypeptide

<400> SEQUENCE: 22

Gly Ser Ser Leu Ala Glu Ala Lys Glu Ala Ala Asn Ala Glu Leu Asp
1               5                   10                  15

Ser Tyr Gly Val Ser Asp Phe Tyr Lys Lys Leu Ile Glu Lys Ala Lys
            20                  25                  30

Thr Val Glu Gly Val Glu Ala Leu Lys Asp Glu Ile Leu Ala Ala Leu
        35                  40                  45

Pro

<210> SEQ ID NO 23
<211> LENGTH: 49
<212> TYPE: PRT

-continued

```
<213> ORGANISM: Artificial
<220> FEATURE:
<223> OTHER INFORMATION: Engineered albumin binding polypeptide

<400> SEQUENCE: 23

Gly Ser Ser Leu Ala Glu Ala Lys Glu Ala Ala Asn Ala Glu Leu Asp
1               5                   10                  15

Ser Tyr Gly Val Ser Asp Phe Tyr Lys Lys Leu Ile Glu Lys Ala Lys
            20                  25                  30

Thr Val Glu Gly Val Glu Ala Leu Lys Glu Ala Ile Leu Ala Ala Leu
        35                  40                  45

Pro

<210> SEQ ID NO 24
<211> LENGTH: 49
<212> TYPE: PRT
<213> ORGANISM: Artificial
<220> FEATURE:
<223> OTHER INFORMATION: Engineered albumin binding polypeptide

<400> SEQUENCE: 24

Gly Ser Ser Leu Ala Glu Ala Lys Glu Ala Ala Asn Ala Glu Leu Asp
1               5                   10                  15

Ser Tyr Gly Val Ser Asp Phe Tyr Lys Lys Leu Ile Glu Lys Ala Lys
            20                  25                  30

Thr Val Glu Gly Val Glu Ala Leu Lys Glu Glu Ile Leu Ala Ala Leu
        35                  40                  45

Pro

<210> SEQ ID NO 25
<211> LENGTH: 49
<212> TYPE: PRT
<213> ORGANISM: Artificial
<220> FEATURE:
<223> OTHER INFORMATION: Engineered albumin binding polypeptide

<400> SEQUENCE: 25

Gly Ser Ser Leu Ala Glu Ala Lys Glu Ala Ala Asn Ala Glu Leu Asp
1               5                   10                  15

Ser Tyr Gly Val Ser Asp Phe Tyr Lys Ser Leu Ile Asp Lys Ala Lys
            20                  25                  30

Thr Val Glu Gly Val Glu Ala Leu Lys Asp Ala Ile Leu Ala Ala Leu
        35                  40                  45

Pro

<210> SEQ ID NO 26
<211> LENGTH: 49
<212> TYPE: PRT
<213> ORGANISM: Artificial
<220> FEATURE:
<223> OTHER INFORMATION: Engineered albumin binding polypeptide

<400> SEQUENCE: 26

Gly Ser Ser Leu Ala Glu Ala Lys Glu Ala Ala Asn Ala Glu Leu Asp
1               5                   10                  15

Ser Tyr Gly Val Ser Asp Phe Tyr Lys Asn Leu Ile Asp Lys Ala Lys
            20                  25                  30

Thr Val Glu Gly Val Glu Ala Leu Lys Asp Ala Ile Leu Ala Ala Leu
        35                  40                  45

Pro
```

```
<210> SEQ ID NO 27
<211> LENGTH: 49
<212> TYPE: PRT
<213> ORGANISM: Artificial
<220> FEATURE:
<223> OTHER INFORMATION: Engineered albumin binding polypeptide

<400> SEQUENCE: 27

Gly Ser Ser Leu Ala Glu Ala Lys Glu Ala Asn Ala Glu Leu Asp
1               5                   10                  15

Ser Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala Leu
        35                  40                  45

Pro

<210> SEQ ID NO 28
<211> LENGTH: 49
<212> TYPE: PRT
<213> ORGANISM: Artificial
<220> FEATURE:
<223> OTHER INFORMATION: Engineered albumin binding polypeptide

<400> SEQUENCE: 28

Gly Ser Ser Leu Ala Glu Ala Lys Val Leu Ala Asn Arg Glu Leu Asp
1               5                   10                  15

Lys Tyr Gly Val Ser Asp Phe Tyr Lys Arg Leu Ile Asn Lys Ala Lys
            20                  25                  30

Thr Val Glu Gly Val Glu Ala Leu Lys Leu His Ile Leu Ala Ala Leu
        35                  40                  45

Pro

<210> SEQ ID NO 29
<211> LENGTH: 26
<212> TYPE: PRT
<213> ORGANISM: Artificial Sequence
<220> FEATURE:
<223> OTHER INFORMATION: Engineered albumin binding polypeptide
<220> FEATURE:
<221> NAME/KEY: MISC_FEATURE
<222> LOCATION: (11)..(11)
<223> OTHER INFORMATION: Xaa is selected from D and E
<220> FEATURE:
<221> NAME/KEY: MISC_FEATURE
<222> LOCATION: (24)..(24)
<223> OTHER INFORMATION: Xaa is selected from D and E
<220> FEATURE:
<221> NAME/KEY: MISC_FEATURE
<222> LOCATION: (25)..(25)
<223> OTHER INFORMATION: Xaa is selected from A and E

<400> SEQUENCE: 29

Gly Val Ser Asp Phe Tyr Lys Lys Leu Ile Xaa Lys Ala Lys Thr Val
1               5                   10                  15

Glu Gly Val Glu Ala Leu Lys Xaa Xaa Ile
            20                  25

<210> SEQ ID NO 30
<211> LENGTH: 20
<212> TYPE: PRT
<213> ORGANISM: Artificial Sequence
<220> FEATURE:
<223> OTHER INFORMATION: Engineered albumin binding polypeptide
<220> FEATURE:
```

```
<221> NAME/KEY: MISC_FEATURE
<222> LOCATION: (3)..(3)
<223> OTHER INFORMATION: Xaa is selected from C, E, Q and S
<220> FEATURE:
<221> NAME/KEY: MISC_FEATURE
<222> LOCATION: (6)..(6)
<223> OTHER INFORMATION: Xaa is selected from C, E and S
<220> FEATURE:
<221> NAME/KEY: MISC_FEATURE
<222> LOCATION: (7)..(7)
<223> OTHER INFORMATION: Xaa is selected from A and S
<220> FEATURE:
<221> NAME/KEY: MISC_FEATURE
<222> LOCATION: (10)..(10)
<223> OTHER INFORMATION: Xaa is selected from A, R and S
<220> FEATURE:
<221> NAME/KEY: MISC_FEATURE
<222> LOCATION: (14)..(14)
<223> OTHER INFORMATION: Xaa is selected from A, C, K and S
<220> FEATURE:
<221> NAME/KEY: MISC_FEATURE
<222> LOCATION: (15)..(16)
<223> OTHER INFORMATION: Albumin binding motif
<220> FEATURE:
<221> NAME/KEY: MISC_FEATURE
<222> LOCATION: (17)..(17)
<223> OTHER INFORMATION: Xaa is selected from A and K
<220> FEATURE:
<221> NAME/KEY: MISC_FEATURE
<222> LOCATION: (18)..(18)
<223> OTHER INFORMATION: Xaa is selected from A, E and S

<400> SEQUENCE: 30

Leu Ala Xaa Ala Lys Xaa Xaa Ala Asn Xaa Glu Leu Asp Xaa Tyr Leu
1               5                   10                  15

Xaa Xaa Leu Pro
            20
```